United States Patent [19]

Federoff

[11] Patent Number: 4,732,856
[45] Date of Patent: Mar. 22, 1988

[54] TRANSPOSABLE ELEMENTS AND PROCESS FOR USING SAME

[75] Inventor: Nina V. Federoff, Baltimore, Md.

[73] Assignee: Carnegie Institution of Washington, Washington, D.C.

[21] Appl. No.: 596,224

[22] Filed: Apr. 3, 1984

[51] Int. Cl.[4] .................... C12N 15/00; C12Q 1/68; C07H 15/12

[52] U.S. Cl. .................................. 435/172.3; 435/6; 435/320; 536/27; 935/1; 935/30; 935/56; 935/67

[58] Field of Search ............... 435/68, 317, 172.3; 935/1, 30, 56, 64, 67; 47/58; 436/63, 94

[56] References Cited

PUBLICATIONS

Baker et al., 1986, Proc. Natl. Acad. Sci. USA 83:4844–4848.
Fedoroff et al., 1983, "Isolation of the Transposable Maize Controlling Elements Ac and Ds", *Cell* v35 235–242.
Geiser et al., 1982, "Genomic Clones of a Wild-Type Allele and a Transposable Element-Induced Mutant Allele . . . ", *Embo J.* V1 1455-1460.
Calos et al., 1980, "Transposable Elements", *Cell* v 20 pp. 579–595.
Searles et al., 1982, "Molecular Cloning of Sequences from a Drosophila RNA Polymerase . . . ", *Cell,* v31 585–592.
Döring et al., 1981, "Transposable Element Ds at the Shrunken Locus in *Zea Mays*", *Mol Gen Genet* v184(3) 377–380.
Burr et al., 1982, "Ds Controlling Elements of Maize at the Shrunken Locus are Large and Dissimilar Insertions", *Cell* v29, 977–986.
Courage-Tebbe et al., 1983, "The Controlling Element Ds at the *Shrunken* Locus in *Za Mays* . . . ", *Cell* v34, 383–393.
Shure et al., 1983, "Molecular Identification and Isolation of the *Waxy* Locus in Maize", *Cell* v35, 225–233.
Döring et al., 1984, "Barbara McClintock's Controlling Elements: Now at the DNA Level", *Cell* v39, 253–259.
Pohlman et al., 1984, "The Nucleotide Sequence of the Maize Controlling Element Activator & Correction", *Cell* v37, pp. 635–643 and *Cell* v39, p. 417.
Sheldon et al., 1983, "Isolation and Analysis of a Genomic Clone Encoding Sucrose Synthetase . . . ", *Mol Gen Genet* v190, 421–426.
Fedoroff et al., 1984, "Cloning of the *Bronze* Locus in Maize by a Simple and Generalizable Procedure . . . ", Proc. Natl. Acad. Sci., v81, 3825–3829.
Marx, 1983, "A Transposable Element of Maize Emerges", *Science,* v219, pp. 829–830 (Feb.).

*Primary Examiner*—Charles F. Warren
*Assistant Examiner*—David T. Fox
*Attorney, Agent, or Firm*—Sughrue, Mion, Zinn, Macpeak and Seas

[57] ABSTRACT

Transposable elements isolated from maize and a process for using the same to identify and isolate genes and to insert desired gene sequences into plants in a heritable manner.

20 Claims, 12 Drawing Figures

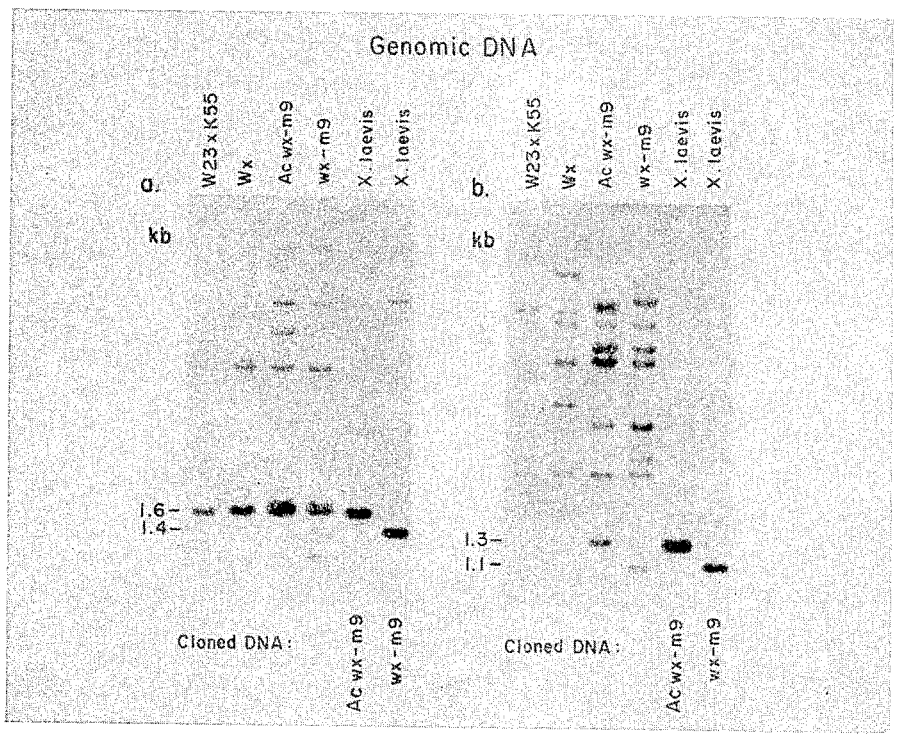
FIG. 8
FIG. 9
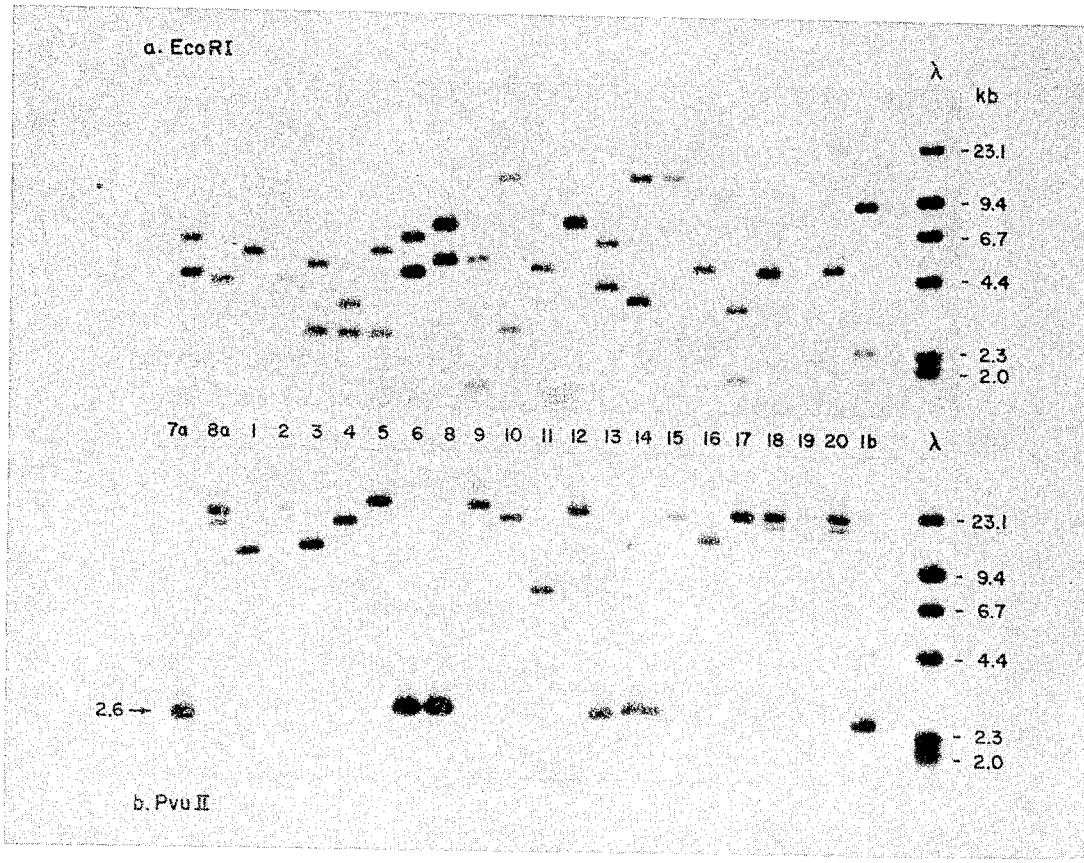

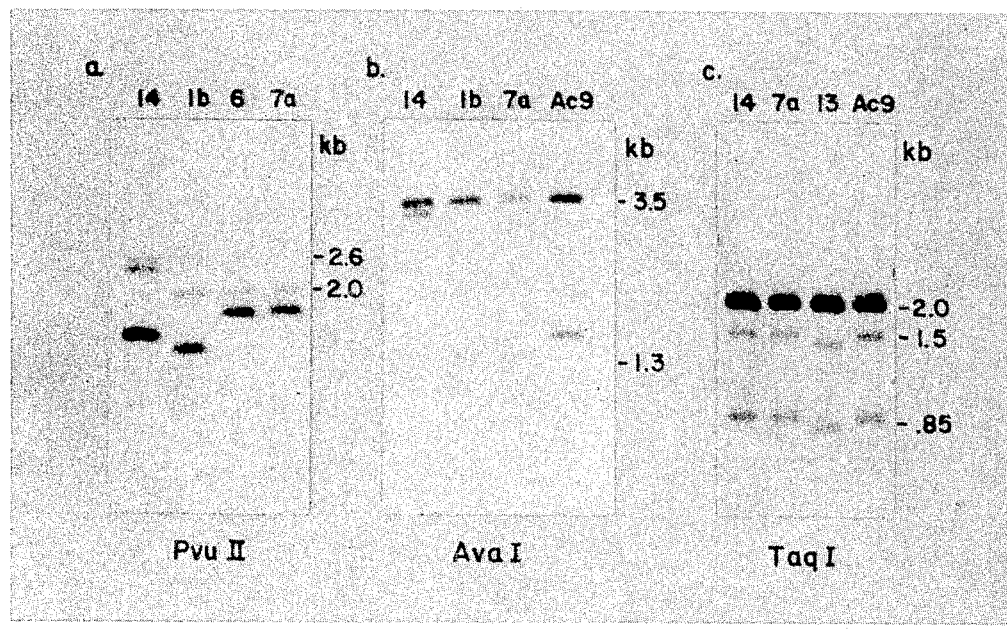
FIG. 10
FIG. 11
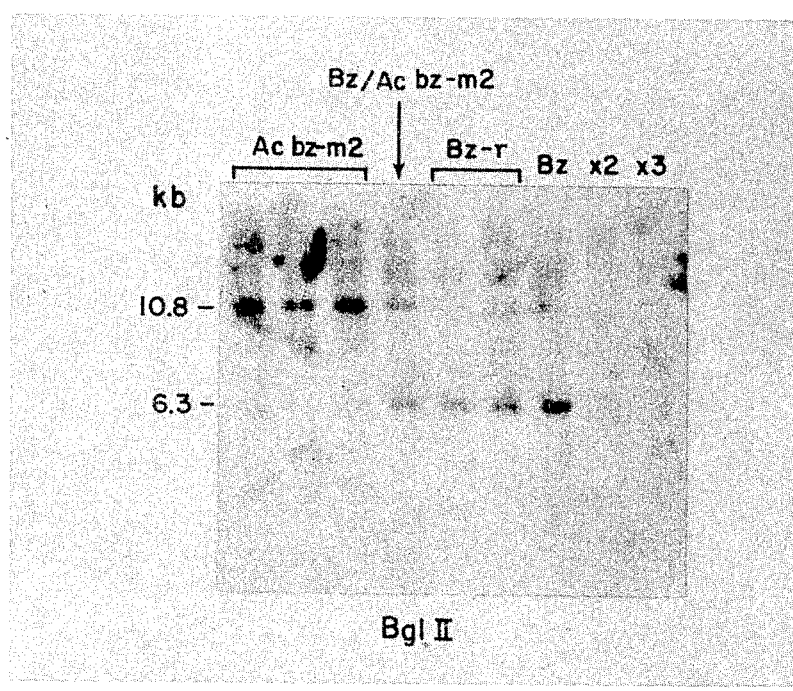

TRANSPOSABLE ELEMENTS AND PROCESS FOR USING SAME

The United States of America has rights to this invention pursuant to National Science Foundation Grant PCM-8307708 and U.S. Department of Agriculture Grant 82-CRCR-1-1065.

FIELD OF THE INVENTION

The present invention relate to transposable elements isolated from maize and a process for using the same to identify and isolate genes and to insert desired gene sequences into plants in a heritable manner.

BACKGROUND OF THE INVENTION

Transposable elements (hereinafter "transposons") are natural gene transfer vectors in bacteria, yeast, *Drosophila melanogaster* and other organisms. The best documented examples of transposons in bacteria are those carrying genes that confer antibiotic resistance on the bacterium in which they reside. These transposons tend to accumulate and become a part of bacterial plasmids. The biological properties of the plasmids permit the spread of the plasmids and their passengers, e.g., drug resistance transposons, in bacterial populations.

In higher organisms, transposons have been, or are being, used in several ways. For example, transponsons are used as mutagens on the Ti plasmid of *Agrobacterium tumefaciens*. That is, a method for using bacterial transposons to cause insertion mutuations in the *Agrobacterium tumefaciens* Ti plasmid, the causative agent of crown gall disease in dicotyledonous plants, has been developed. (See Zambriski, P., Goodman, H., Van Montagu, M. and Schell, J., *Mobile Genetic Elements*, J. Shapiro, Ed., (Academic Press) New York, pp. 506–535 (1983)). By this technique, it has become possible to identify the plasmid-borne genes that are responsible for virulence, as well as those that are responsible for the tumorous transformation of plant cells caused by the Ti plasmid. Further, it has become possible to show by using transposable elements, that a portion of the Ti plasmid can be integrated into plant genomes and can act as a vehicle for transferring genes from virtually any organism to any dicotyledonous plant that is susceptible to *Agrobacterium tumefaciens*.

Transposons have also been used to identify and isolate otherwise inaccessible genes (See Bingham, P. M., Kidwell, M. G. and Rubin, G. M., *Cell* 29:995–1004 (1982)). That is, the *White* locus of *Drosphilia melanogaster* has been isolated by virtue of the existence of an insertion mutution at the locus caused by a transposon that has been isolated and studied using recombinant DNA technology. Such applications are receiving increasing attention in plants and animals.

The use of transposable elements as deliberate gene transfer vectors evolved from work in bacteria and yeast and, as stated above, has recently been developed into a useful research tool in *Drosolphila melanogaster* (See Rubin, G. M. and Spradling, A. C., *Science* 218:348–353 (1982)). The basic principle on which such applications are based is that transposons are compact genetic units that contain within their sequences essentially all of the coding information required for transposition. Although the transposition functions are only now beginning to be identified in higher organisms, in bacteria, they are known to include enzymes termed transposases, as well as molecules which regulate expression of the transposase and other genes encoding transposition-specific proteins.

In maize, a monocotyledon, transposable elements were first genetically identified in the mid-1940s. These elements have been studied extensively and their genetic behavior has been extensively reviewed (See McClintock, B., *Cold Spring Harbor Symp. Quant. Biol.* 16:13–47 (1951); McClintock, B., *Cold Spring Harbor Symp. Quant. Biol.* 21:197–216 (1956); McClintock, B., *Brookhaven Symp. Biol.* 18:162–184 (1965); Fincham, J. R. S. , and Sastry, G. R. K., *Ann. Rev. Genet.* 8:15–50 (1974); and Fedoroff, N., *Mobile Genetic Elements*, J. Shapiro, Ed., (Academic Press) New York, pp. 1–63 (1983)).

It has been demonstrated that transposons are normal, although cryptic, residents of the maize genome and that upon activation, they are responsible for various types of genetic rearrangements, including chromosome breakage, deletions, duplications, inversions and translocations. In addition, it has been shown that certain common types of unstable mutations, which have been studied for decades in both maize and in other organisms, are attributable to the insertion of transposons into genes or genetic loci.

Currently, there is a great deal of interest in the development of gene transfer vectors for use with agriculturally important plants (See Outlook for *Science and Technology, The Next Five Years*, Vol. III (*National Science Foundation* (1982); and *O.T.A. Report, Impact of Applied Genetics* (1981)).

Although the United States presently has an excess productivity in the agricultural sector, this is recognized as a local and short term condition. Thus, agricultural research and planning must be based on long term considerations. The variety of problems surrounding increases in population, degradation of prime farm land and decreasing availability of good farm land necessitates the increased use of marginal land, as well as exogenous fertilizers and chemical pest control compositions.

Classical plant breeding programs have thus far been successful in increasing agricultural productivity. However, a substantial fraction of the increase in farm productivity experienced in the United States in the past 40 years is attributable to the use of fertilizers and modern energyintensive cultivation practices, both of which are increasingly costly. The ability of plant breeding alone to sustain productivity is a matter of some question. Plant breeders are divided in their views on whether genetic improvements will continue at the rate that has occurred over the past few decades or will begin to level out. Since such questions cannot be resolved a priori, it is prudent to explore a variety of additional means by which agronomically useful traits can be accumulated and improved in major crop plants. The unconventional areas that are presently receiving the most attention in the academic research establishment, as well as in both small and large firms with plant-oriented research programs are wide genetic crosses, tissue culture and the development of gene transfer systems that circumvent fertility barriers.

In the past, many attempts have been made to transsfrom plant cells with DNA from a variety of sources. The first unequivocal demonstration that DNA transfer can and does occur in plants emerged from the work described above on *Agrobacterium tumefaciens* Ti plasmid. However, Ti-plasmid mediated gene transfer is presently accomplished only in dicotyledonous plants that interact with the plasmid's natural host bacterium. Since most major crop species are monocotyledonous, ti-plasmid mediated gene transfer has limited applications.

SUMMARY OF THE INVENTION

Accordingly, an object of the present invention is to isolate and characterize transposons from maize.

An additional object of the present invention is to provide plasmids containing trasposable elements from maize.

A further object of the present invention is to provide a method of identifying and isolating scientifically and agronomically important genes from plants.

Another object of the present invention is to provide a method for inserting desired genes into plants in a heritable manner.

The above objects of the present invention have been met by the isolation and use of the previously genetically identified but unisolated transposons: Activator9 (hereinafter "Ac9"), Dissociation9, Dissociation6 (hereinafter "Ds9" and "Ds6", respectively), other Ac transposons, Mp and Suppressor-mutator (hereinafter "Spm").

BRIEF DESCRIPTION OF THE DRAWINGS

FIG. 8 shows an autoradiogram of a blot hybridization analysis of genomic maize DNAs digested with restriction nuclease Hind III (FIG. 8a) and Pvu II and Eco RI (FIG. 8b).

FIG. 9 shows an autoradiogram of a blot hybridization analysis of recombinant λ phage DNAs to the internal Hind III fragment of pAc9.

FIG. 10 shows an autoradiogram of a blot hybridization analysis of recombinant λ clones digested with Pvu II, Ava I and Taq I probed with $^{32}P$-labeled fragments of Ac9 DNA.

FIG. 11 shows an autoradiogram of a blot hybridization analysis of a cloned Pst I fragment derived from the sequence flanking the Ac element in λAcbzm2-7a to maize genomic DNAs.

DETAILED DESCRIPTION OF THE INVENTION

Figure 1:
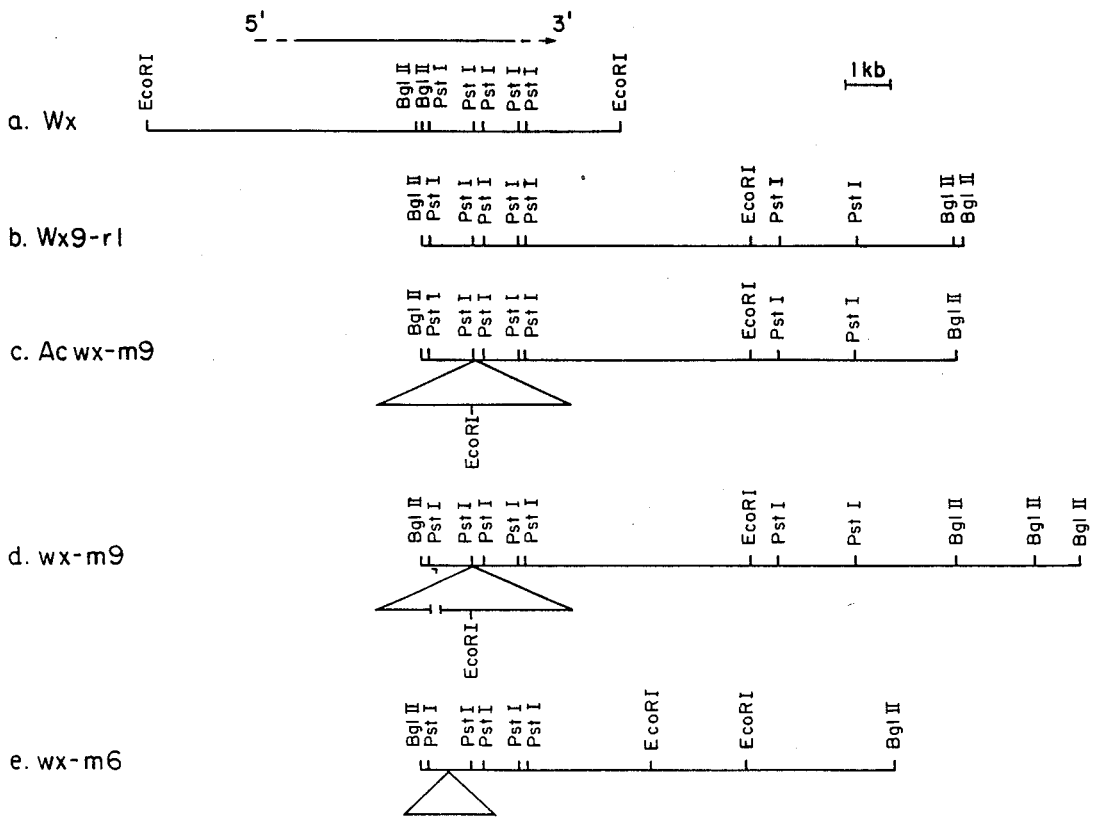
FIG. 1 shows restriction nuclease maps of the Wx locus cloned from maize strains carrying various alleles of the Wx locus.

As stated above, the present invention relates to transposons derived from maize which when essentially pure can be employed to identify and isolate genes from plants and to insert desired genes into plants in a heritable manner.

Examples of plants which can be employed in the present invention include maize, tobacco, tomato, petunias, wheat, rye and other cereal grains.

Examples of the essentially pure transposons isolated from maize include the previously genetically identified yet unisolated Ac9, Ds9 and Ds6 transposons. The isolation method of the present invention can be extended to other known Ac transposons, as well as other transposons such as Mp and Spm.

These transposons are reproduced and usefully employed as cloning vectors when integrated in plasmids such as pKP32, pUC8, pBR325, and pBR322, as well as other well known cloning vehicles such as bacteriophage DNAs, plant viral DNAs, and animal viral DNAs.

The method for identifying and isolating genes from plants in accordance with the present invention comprises: (1) isolating genomic DNA from a plant that is carrying a transposon insertion mutation at the locus to be isolated; (2) cloning fragments of the genomic DNA of step (1); (3) probing the cloned fragments of step (2) with DNA sequence from a transposon derived from maize so as to select for cloned fragments homologous to the transposon; (4) subcloning the sequences flanking the transposon from the clone selected out in step (3); (5) probing genomic DNA fragments from plants that carry mutant and non-mutant alleles of the locus to be isolated with the subclone of step (4) so as to identify a subclone containing the locus to be isolated; (6) cloning genomic DNA fragments from plants that carry a non-mutant allele of the locus to be isolated; and (7) probing the resulting clones of step (6) with the subclone of step (5) so as to isolate the locus.

Examples of mutant alleles of a locus to be isolated are not limited and can include loci of unknown biochemical function, such as the P and R loci of maize, for which Ac insertion alleles have already been identified (See Brink, R. A. and Nilan, R. A., *Genetics* 37:519–544 (1952); Barclay, P. C. and Brink, R. A., *Proc. Natl. Acad. Sci. USA* 40:1118–1126 (1954); William, E. and Brink, R. A., *Genetics* 71:97–100 (1972); and Brink, R. A. and Williams, E., *Genetics* 73:273–296 (1973)). In addition, the method of the present invention can be used to isolate any locus from which a new Ac insertion mutation is identified.

The method of employing transposons to insert desired genes into plants of the present invention comprises (1) cloning a gene to be transferred into a transposon derived from maize or derivative thereof (hereinafter "gene transfer vector"), and (2) transforming a plant, plant cell or plant protoplast with (a) the gene transfer vector of step (1), and (b) a transposon possessing an active transposase.

Examples of transposons derived from maize and derivatives thereof are desribed below in more detail in Examples 1 and 3, respectively.

The gene transfer vectors can be introduced into plants by germinating pollen in the presence of the transfer vector. the pollen is used to fertilize the female gametophyte. The gene transfer vector may also be introduced into the reproductive cells of the plant by other means such as, for example, direct injection or on viral DNA.

Furthermore, the gene transfer vectors can be introduced into, i.e., transform, plant cells or protoplasts by means of, for example, injection and liposome-mediated transfer.

The Ac transposon of the present invention transposes autonomously. That is, mutations caused by insertion of this element in or near a locus are unstable, reverting both somatically and germinally at a high frequency by transposition of the element away from the locus. On the other hand, the Ds element, which was initially identified as a site of chromosome dissociation or breakage (See McClintock, B., *Carnegie Inst. of Wash. Year Book* 44:108–112 (1945); McClintock, B., *Carnegie Inst. of Wash. Year Book* 45:176–186 (1946); McClintock, B., *Carnegie Inst. Of Wash. Year Book* 46:146–152 (1947); and McClintock, B., *Carnegis Inst. of Wash. Year Book* 47:155–169 (1948)), has been designated as a non-autonomous element (See Fedoroff, N., *Mobile Genetic Elements*, J. Shapiro, Ed., (Academic Press) New York, pp. 1–63 (1983). That is, the Ds transposon requires the presence of the autonomous Ac transposon for both transposition and chromosome breakage (See McClintock, B., *Cold Spring Harbor Symp. Quant. Biol.* 16:13–47 (1951)).

The observation that Ac insertion alleles of a locus can give rise directly to Ds-like mutations at the same locus raised the possibility that the Ds and Ac elements are structurally related (See McClintock, B., *Carnegie Inst. of Wash. Year Book* 54:245–255 (1955); McClintock, B., *Cold Spring Harbor Symp. Quant. Biol.* 21:197–216 (1956); McClintock, B, *Carnegie Inst. of Wash. Year Book* 55:323–332 (1956); McClintock, B., *Carnegie Inst. of Wash. Year Book* 61:448–461 (1962); and McClintock, B., *Carnegie Inst. of Wash. Year Book* 62:486–493 (1963)).

Several unstable mutant alleles of the Wx locus which are either Ac or Ds insertion mutations have been isolated (See Fincham, J. R. S. and Sastry, G. R. K., *Ann. Rev. Genet.* 8:15–50 (1974)). Of the available alleles, the Acwx-m9, wx-m9 and wx-m6 alleles were employed in order to isolate the transpons of the present invention because of their genetic history and molecular properties although other well known Ac insertion alleles, such as Acbz-m5, could also be used to isolate other Ac transposons from maize. (See McClintock, B., *Carnegie Inst. of Wash. Year Book* 51:212–219 (1952); McClintock, B., *Carnegie Inst. of Wash. Year Book* 62:486–493 (1963); and Fincham, J. R. S. and Sastry, G. R. K., *Ann. Rev. Genet.* 8:15–50 (1974)).

EXAMPLE 1

Isolation of Transposons

1. Maize Strains

The maize strains employed in the isolation of the transposons of the present invention include the W23xK55 hybrid and strains containing the Acwx-m9, wx-m9 and wx-m6 alleles. The W23xK55 hybrid was obtained from E. H. Coe. The W23 strain is available from the University of Wisconsin Agricultural Experimental Station in Madison, Wisc. while the K55 strain is available from the Kansas Agricultural Experimental Station in Manhattan, Kans. Strains containing the Acwx-m9, wx-m9 and wx-m6 alleles were obtained from B. McClintock and are available from the Maize Coop Stock Center in Urbana, Ill.

The Acwx-m9 allele originated by transposition of the Ac element from the Bronze locus, which is distal to the Wx locus on the short arm of chromosome 9 (See McClintock, B., *Carnegie Inst. of Wash. Year Book* 62:486–493 (1963)). The phenotype of the Acwx-m9 allele is intermediate between the dominant Wx and the recessive wx alleles. The Acwx-m9 allele reverst both frequently and relatively early in endosperm development producing endosperm tissue that shows variegation for the Wx phenotype and the intermediate phenotype characteristic of the Acwx-m9 allele. A germinally stable Wx revertant, i.e., Wx9-rl was employed in identifying the transposons of the present invention.

The wx-m9 allele is a derivative of the Acwx-m9 allele (See McClintock, B., *Carnegie Inst. of Wash. Year Book* 62:486–493 (1963)). The wx-m9 allele shows the intermediate phenotype of the Acwx-m9 allele but is unstable only in the presence of an Ac transposon elsewhere in the genome. The wx-m9 derivative of the Acwx-m9 allele therefore shows the genetic behavior characteristic of a Ds insertion mutation (See McClintock, B., Id.). The wx-m9 allele was selected for the present purpose because of its derivation from and phenotypic similarity to the Acwx-m9 allele.

The wx-m6 allele was employed because it arose, albeit indirectly, by transposition of the Ds element to the Wx locus from a site proximal to the Wx locus (See McClintock, B., *Carnegie Inst. of Wash. Year Book* 46:146–152 (1947); McClintock, B., *Carnegie Inst. of Wash. Year Book* 47:155–169 (1948); and McClintock, B., *Carnegie Inst. of Wash. Year Book* 51:212–219 (1952)). The same Ds element is responsible for the unstable mututions at the Shrunken locus that have been previously studied (See McClintock, B., *Carnegie Inst. of Wash. Year Book* 51:212–219 (1952); *Carnegie Inst. of Wash. Year Book* 52:227–237 (1953); Burr, B. and Burr, F. A., *Cold Spring Harbor Symp. Quant. Biol.* 45:463–465; Burr, B. and Burr, F. A., *Genetics* 98:143–156 (1981); Burr, B. and Burr, F. A., *Cell* 29:977–986 (1982); Geiser et al, *EMBO J.* 1:1455–1460 (1982); Federoff et al, *J. Mol. Appl. Gen.* 2:11–29 (1983); and Courage-Tebbe et al, *Cell* 34:383–393 (1983)). There is evidence that the Ds insertion site in the wx-m6 is within the protein coding sequence of the Wx locus. The site of insertion is between two mutations that give altered structural proteins (See Nelson, O. E., *Genetics* 60:507–524 (1968); and Echt, C. S. and Schwartz, D., *Genetics* 99:275–284 (1981)). Moreover, it has been demonstrated that somatic reversion of the wx-m6 allele in the presence of an Ac element results in the synthesis of an abnormal Wx protein (See Shure, M., Wessler, S. and Fedoroff, N., *Cell* 35:225–233 (1983).

The above described strains were either homozygous or heterozygous for the mutant or revertant allele of the Wx locus. Homozygotes were obtained by outcrossing plants that were heterozygous for a stable Wx allele and the unstable allele of interest to Wx/Wx or Wx/wx plants and then recovering the unstable allele by self-pollination of plants grown from Wx kernels.

Appropriate genetic tests were carried out to verify the genetic identity of the alleles present in plants with Ds mutations, but lacking an Ac transposon. That is, plants carrying the alleles were crossed to or by plants that were homozygous for a stable recessive allele of the Wx locus which carried an Ac transposon. The presence of a Ds mutation at the Wx locus was determined by the appearance of Wx sectors in kernels receiving the mutant allele and an active Ac transposon.

Wx revertants were selected as single kernels showing a Wx phenotype throughout the endosperm on ears of plants homozygous for the Acwx-m9 allele or heterozygous for the Acwx-m9 allele and a stable wx allele.

Plants grown from Wx kernels were self-pollinated, tested for the presence of Ac and for Ac-activated breakage of the short arm of chromosome 9, with concomitant loss of the Wx locus during endosperm development. The presence of an Ac transposon was determined by crossing the plant to a plant that had a Ds transposon proximal to the Wx locus and additional markers on the same chormosome, i.e., C-I, Sh and Bz, whose loss could be monitored phenotypically following breakage of the chromosome carrying the Ds transposon in the presence of an Ac transposon. Chromosome breakage was tested by crossing the plants to plants that contained an Ac transposon and were homozygous for a stable recessive wx allele and checking for the appearance of wx sectors in kernels heterozygous for the Wx-9rl and wx alleles.

The Wx9-rl allele is a spontaneous revertant derived from the Acwx-m9 allele and is available from the Maize Coop Stock Center in Urbana, Ill. As discussed below, the Wx9-rl allele shows no evidence of the presence of either an Ac or a Ds element at the Wx locus.

2. Isolation from Maize Strains of Genomic Maize DNA used for Cloning

Genomic maize DNA was isolated from 5-day etiolated seedlings, 3 week-old plants or the inner leaves and immature tassels of 6 week-old plants. Frozen plant tissue was pulverized in a mortar with crushed siliconized glass in the presence of liquid nitrogen. The powdered plant tissue was taken up in 8.0 ml/g of a cold (0–4° C.) lysis buffer containing 8.0 M urea, 0.35 M NaCl, 0.05 M Tris-HCl (pH 7.5), 0.02 M EDTA, 2.0% sarcosyl and 5.0% phenol. The mixture was stirred gently with a glass rod until homogeneous and then mixed with one volume of a 3:1 (by volume) mixture of phenol and chloroform containing 5.0% (by volume) isoamyl alcohol at room temperature. Sodium dodecylsulfate was also added to a final concentration of 0.5% by volume. The mixture was warmed to room temperature and gently shaken for 10 minutes. The organic and aqueous phases were separated by low speed centrifugation and the above-referred to phenol-chloroformisoamyl alcohol extraction was repeated twice. The salt concentration was increased by the addition of 1/20 volume of 3.0 M sodium acetate and the genomic maize DNA was spooled out after the addition of 2 volumes of cold ethanol (−20° C.). The genomic maize DNA was immediately and gently resuspended in approximately 1/5 of the orginal lysis volume of 10 mM Tris-HCl (pH 7.5), 10 mM EDTA. The genomic maize DNA was banded twice in a CsCl-ethidium bromide gradient prepared by adding 1.0 g solid CsCl for each ml of DNA solution and adding ethidium bromide to a final concentration of 200 μg/ml. The ethidium bromide was removed by extraction with an equal volume of CsCl-saturated isopropanol and the genomic maize DNA was dialyzed against 10 mM Tris-HCl (pH 7.5), 1.0 mM EDTA (hereinafter "TE").

3. Fragmenting Genomic Maize DNA

Total genomic maize DNA was digested with Eco RI or Bgl II (Bethesda Research Laboratories (BRL)) using 5.0 units of enzyme per μg of DNA under conditions specified by the enzyme supplier. Although internal controls indicated that digestion of $P^{32}$ labeled phage λ DNA was complete under the conditions used, some of the cloned fragments obtained had internal Bgl II sites. This may be attributable to the fact that certain Bgl II sites in genomic maize DNA are only partially cleaved in some plants or to the simultaneous cloning of non-contiguous fragments.

4. Cloning of Genomic Maize DNA Fragments

The cloning procedures and vectors analyzed were those described by Shure, M., Wessler, S. and Fedoroff, N., Cell 35:235–242 (1983), except that cloning vector λEMBL4 was digested with Bam HI (BRL) or Eco RI and Sal I (BRL) prior to isolation of ligated vector arms as described below. Other cloning vectors can be used in the present invention such as λ1059, Ch4 and Ch8.

λEMBL4 phage (See Frischauf, A.-M, Lehrech, H., Poustaka, A. and Murray, N., J. Mol. Biol. 170:827–842 (1983)) was grown in strains Q358 (See Karn et al, Proc. Natl. Acad. Science USA 77:5172–5176 (1980)) or K803 (LE392) (Maniatis, T., et al, Molecular Cloning (Cold Spring Harbor Press) Cold Spring Harbor, N.Y., p. 504 (1982)) in NZCYM medium (See Maniatis et al, Id.). Phage and phage DNA were purified by modification of the procedures described by Yamamoto et al, Virology 40:734–744 (1970). The phage were pelleted through a glycerol step gradient, treated with RNase and DNase and then banded in a CsCl step gradient as described in Maniatis, T., et al, Molecular Cloning (Cold Spring Harbor Press) Cold Spring Harbor, N.Y. p. 84 (1982). Phage DNA was purified as described by Maniatis, T., Id., p. 85. The sticky ends of the purified linear phage DNA were self-annealed at 42° C. in 132 mM Tris-HCl (pH 7.5), 13 mM MgCl$_2$, 0.8 mM rATP and 20 mM dithiothreitol (DTT) for one hour. The solution was then diluted two-fold. Next, T4 DNA ligase (BRL) was added using 1.5 units/100 μg DNA and the mixture was incubated at 12° C. overnight. Thereafter, the ligated vector was cleaved using Bam HI (BRL) or Eco RI (BRL), 4.0 units/μg DNA, for 3 hours followed by digestion with Sal I (BRL) using 4.0 units/μg DNA under conditions specified by the enzyme supplier. The digests were sequentially phenol extracted, ether extracted, dialyzed against TE and centrifuged through a 10–40% by weight sucrose gradient as described by Maniatis, T., et al, Cell 15:687–701 (1978). Fractions containing the ligated vector arms were detected by agarose gel electrophoresis (See Maniatis, T., et al Id.), pooled, ethanol precipitated, redissolved in TE at a concentration of 0.5 mg/ml and stored frozen.

Total Bgl II-digested genomic maize DNA prepared as described above was ligated into the Bam HI cloning site of λEMBL4 as described below. The 5.0 μl ligation reactions contained a total of 1.0 μg of DNA and the ratio of arms to insert varied between 4:1 and 1:1 by weight. Ligation was carried out a 12° C. overnight in a buffer containing 0.066 M Tris-HCl (pH 7.5), 6.6 mM MgCl$_2$, 0.4 mM rATP, 10 mM DTT and 1.25 units of T4 ligase (BRL). The ligated maize-phage DNA was then packaged in vitro as described in Hohn, B., Methods in Enzymology 68:299–309 (1979). The recombinant phage were plated on E. coli strain K803. The cloning efficiency of total Eco RI or Bgl II digested genomic maize DNA was somewhat lower (2–4×10$^5$ pfu/μg of maize DNA) than that of genomic maize DNA enriched for fragments in the correct size range for cloning, i.e., 9.0 to 22 kb, (1–3×10$^6$ pfu/μg maize DNA). Nonetheless, the resulting recombinant phage were enriched for large maize DNA fragments and yielded 2 or more Wx clones per 10⁵ recombinant phage.

As described by Fedoroff, N., *Maize Genet. Coop. Newsletter* 57:154–155 (1983), λEMBL4 containing genomic maize DNA fragments plated less efficiently by a factor of about 15 on *E. coli* strains Q364 or Q359 than on *E. coli* K803. *E. coli* strains Q364 or Q359 are generally used as selective hosts for propagation of recombinant phage prepared in the λEMBL derivatives of the λ1059 vector (See Karn et al, *Proc. Natl. Acad. Sci. USA* 77:5172–5176 (1980)). Hence, the background of non-recombinant phage was minimized by purification of vector arms, as described above, rather than by genetic selection.

Recombinant phage containing fragments with Ac or Ds insertions were found to grow poorly, invariably producing very small plaques. To ensure that the cloned fragments were representative of the original genomic maize DNA sequences, multiple independent clones were isolated and analyzed. Moreover, restriction nuclease digests of cloned and genomic maize DNAs homologous to Wx locus probes in the mutant strains were compared to verify the identity of the cloned and genomic maize DNA sequences.

5. Identification of Transposon Insertion Sites

Transposon insertion sites were identified by blot hybridization analysis of recombinant phage DNAs using the Eco RI Wx genomic fragment subcloned in pBR322 (FIG. 1a) (See Shure, M., Wessler, S. and Fedoroff, N., *Cell* 35:235–242 (1983)) and by electronmicroscopic analysis of heteroduplexes formed by homologous fragments of the Wx locus cloned from strains having an Ac insertion mutation at the Wx locus as described below.

6. Isolation of the Ac Element in Acwx-m9

In order to identify and isolate the Ac element, the resulting recombinant phage were screened by plaque hybridization (See Benton, W. D. and Davis, R. W., *Science* 196:180–182 (1977)) with the pWx0.4 DNA clone described by Shure, M., Wessler, S. and Fedoroff, N., *Cell* 35:225–233 (1983) which had been labeled with $P^{32}$ by nick-translation (See Maniatis, T., Jeffrey, A. and Kleid, D.G., *Proc. Natl. Acad. Sci. USA* 72:1184–1188 (1975)). Several independent fragments with homology to the pWx0.4 plasmid and having identical inserts were isolated from each of the alleles used.

The Bgl II fragments isolated from DNA of plants carrying the Wx9-rl allele were found to be approximately 12.5 to 13 kb in length, while the Bgl II fragments isolated from plants carrying the Acwx-m9 allele were approximately 17 kb in length. Preliminary restriction nuclease analysis of these fragments revealed that the fragments were quite similar, except that a 0.23 kb Pst I fragment located near the 3' end of the Wx transcription unit (See FIG. 1a) present in the Wx9-rl fragment (See FIG. 1b) was replaced by a novel 4.7 kb Pst I fragment with an internal Eco RI site in the Bgl II fragment cloned from the Acwx-m9 allele (See FIG. 1c). This is illustrated by the results of the blot hybridization experiment shown in FIG. 2.

Figure 2:
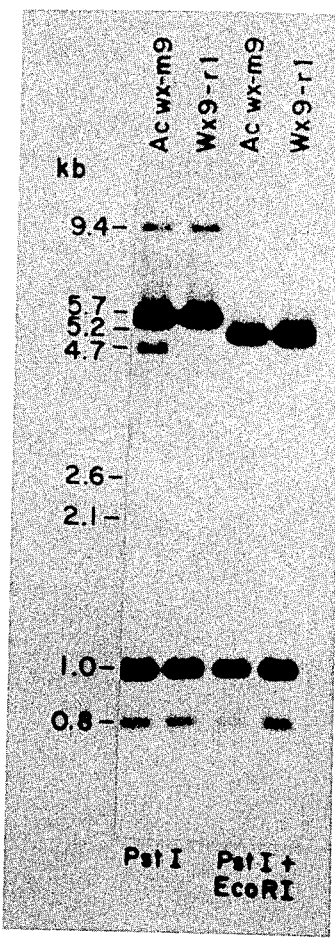
FIG. 2 shows an autoradiogram of a blot hybridization analysis of restriction nuclease Bgl II fragments cloned from genomic maize DNA carrying the Acwx-m9 and Wx9-rl alleles.

Phage DNAs containing the Acwx-m9 and Wx9-rl Bgl II fragments were digested with Pst I or a combination of Pst I and Eco RI, fractionated on a 0.7% agarose gel and transferred to nitrocellulose, as shown by FIG. 2. The blots were hybridized to $P^{32}$-labeled pWx5-8, which comprises the Eco RI Wx genomic fragment cloned in pBR325 (Shure, M., Wessler, S. and Fedoroff, N., *Cell* 35:225–233 (1983)).

The Pst I digest of the Wx9-rl Bgl II fragment contained 2 additional Pst I fragments that were 0.23 and 0.17 kb in length and were not detectable in FIG. 2 because of their size. The 0.23 kb fragment was missing from the Acwx-m9 Bgl II fragment, although the 0.17 kb fragment was present.

The Pst I digest of the Acwx-m9 Bgl II fragment contained a novel 4.7 kb fragment with limited homology to the probe that was not present in the Wx9-rl Bgl II fragment. The Pst I-Eco RI digest of the Acwx-m9 Bgl II fragment contained two shorter fragments of 2.6 and 2.1 kb that were not present in the corresponding digest of the Wx9-rl fragment. Although the 0.23 kb Pst I fragment that gives rise to the novel 4.7 kb Pst I fragment is not apparent in FIG. 2, its presence in the Wx9-rl DNA and its absence in the Acwx-m9 DNA were detected by analyzing Pst I digested genomic maize DNAs on polyacrylamide gels.

Figure 3:
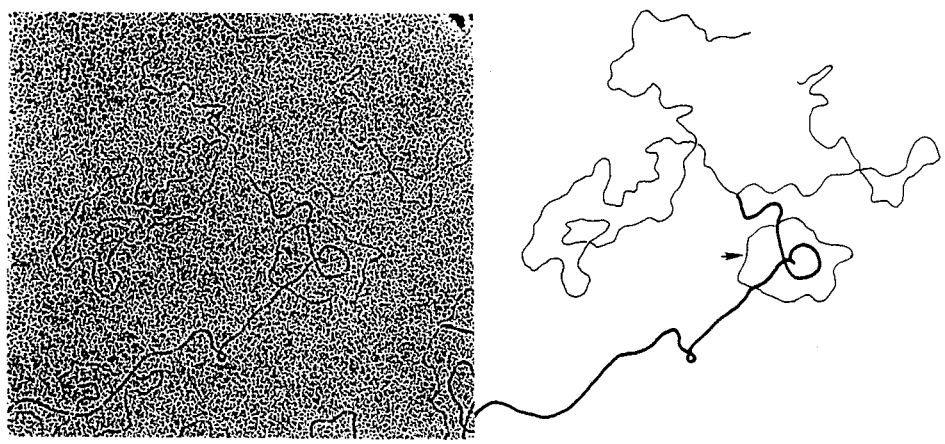
FIG. 3 shows an electron micrograph of a heteroduplex between λEMBL4 phage DNAs containing Wx restriction nuclease Bgl II fragments cloned from genomic maize DNA carrying the Acwx-m9 and Wx9-rl alleles.

The resemblance between the fragments cloned from Acwx-m9 and Wx9-rl shown in FIG. 2 was confirmed by electron microscopic analysis of heteroduplexes formed between phage DNAs carrying the Bgl II fragments cloned from the Acwx-m9 and Wx9-rl alleles in opposite orientations, as shown in FIG. 3. In FIG. 3. Phage DNAs or plasmid DNAs were heteroduplexed and spread for electron microscopic analysis as described by Davis, R. W., Simon, M. and Davidson, N., *Methods in Enzymology*, L. Grossman and K. Moldave, Eds., (Academic Press) New York, 21:413–428 (1971).

As is evident in FIG. 3, wherein recombinant phage DNAs containing Wx locus Bgl II fragments cloned from the Acwx-m9 and Wx9-rl alleles were denatured, partially renatured and spread for electron microscopic analysis, the Bgl II fragments were entirely homologous to each other except in a region near one end. These fragments differed from each other by a sequence of approximately 4.0 kb which was present in one fragment, but not in the other. The loop representing the non-homologous sequence was the same length and occurred at the same distance from the end of the Bgl II insert in all heteroduplexes. This indicated that the non-homologous region was unique.

When the Acwx-m9 Bgl II fragment was heteroduplexed with the Eco RI fragment (FIG. 1a) described by Shure, M., Wessler, S. and Fedoroff, N., *Cell* 35:225–233 (1983), the two fragments were also found to differ by the presence of a 4.0 kb insertion within the region of overlap between the two fragments.

Accordingly, the Acwx-m9 allele yielded a Bgl II fragment of the Wx locus that contained an insertion not present in either of the two corresponding sequences isolated from Wx9-rl and the Wx Eco RI fragment described by Shure et al, Id. Thus, since one of the Wx fragments lacking the insertion present in the Acwx-m9 allele was a stable Wx revertant newly derived from the Acwx-m9 allele, i.e., Wx9-rl, this insertion must correspond to the Ac element causing the unstable Acwx-m9 mutation.

In subsequent detailed mapping experiments, the length of the insertion was determined to be 4.3 kb. Its location is indicated in FIG. 1c. In FIG. 1, the relationship between the Eco RI Wx fragment and the Bgl II fragments cloned from strains carrying the Acwx-m9, wx-m9, wx-m6 and Wx9-rl alleles is indicated by the vertical alignment of the restriction endonuclease cleavage site maps. As indicated by the arrow, the Eco RI fragment contained most or all of the Wx transcription unit. The Bgl II fragments contained only the 3' end of the transcipion unit but included the site of insertion of the Ac and Ds elements in the mutant strains. The location and relative size of the Ac and Ds insertions, whose structure is described above and below, are indicated by the triangles below the fragments.

7. Isolation of the Ds Element in wx-m9

Upon cloning a Bgl II fragment with homology to the pWx0.4 cDNA plasmid from a strain homozygous for the wx-m9 derivative of the Acwx-m9 allele, the fragment was determined to be similar in structure to the Bgl II fragment cloned from the Acwx-m9 allele, but was longer at the right and contained two additional internal Bgl II sites (See FIG. 1d). Restriction nuclease analyses of this fragment revealed the presence of a 4.1 kb insertion within the same 0.23 kb Pst I fragment within which the Ac element was inserted in Acwx-m9. This is illustrated in FIG. 1d.

8. Isolation of the Ds Element in wx-m6

A Bgl II fragment containing part of the Wx transcription unit from a strain homozygous for the wx-m6 allele was cloned. Its structure is shown in FIG. 1e. The Wx allele from which the Wx Eco RI fragment was cloned is the progenitor of the wx-m6 allele (See FIG. 1a). The structure of the wx-m6 transcription unit different from that in the strain containing the progenitor Wx allele by the presence of an insertion in a 1.0 kb Pst I fragment on the 5' side of the insertion site in Acwx-m9 and wx-m9. The insertion, whose length was estimated at 2.4 kb on the basis of blot hybridization data (See Shure, M., Wessler, S. and Fedoroff, N., Cell 35:225-233 (1983)), proved to be 2.0 kb in length. The location and size of the insertion is shown in FIG. 1e.

9. Comparison of Insertions in Acwx-m9, wx-m9 and wx-m6

In order to compare the insertions present in the Acwx-m9, wx-m9 and wx-m6 strains, the Pst I fragments of the Wx locus in which insertions had been identified were subcloned into the pKP32 cloning vector. pKP32 was obtained from K. Peden, and is described in detail in Shure, M., Wessler, S. and Fedoroff, N., Cell 35:225-233 (1983), although a cloning vehicle such as pBR322, pBR325 or pUC8, could also be employed. pKP32 is a derivative of pBR322 from which the Eco RI and Ava I sites have been eliminated and which carries a deletion extending from nucleotide 1651 to nucleotide 2470 of the pBR322 sequence.

Subcloning was carried out by cleaving recombinant λ phage DNA and pKP32 plasmid DNA with Pst I under conditions specified by the supplier (New England Biolabs) and ligating the phage and plasmid DNAs with T4 ligase as described above. The ligated DNAs were transformed into competent HB101 E. coli (See Maniatis, T., et al, Molecular Cloning (Cold Spring Harbor Press) Cold Spring Harbor, N.Y., p. 250 (1982)) and tetracycline resistant colonies were isolated and grown for extraction of plasmid DNA (See Maniatis, T., et al, Molecular Cloning (Cold Spring Harbor Press) Cold Spring Harbor, N.Y., p. 368 (1982)). Plasmids containing the correct Pst I fragments from the recombinant phage were identified by their electrophoretic mobility on agarose gels.

The plasmids containing the insertion-bearing Pst I fragments subcloned from Acwx-m9, wx-m9 and wx-m6 Bgl II genomic maize DNA fragments were designated pAc9, pDs9 and pDs6, respectively. The transposons of the present invention have been designated Ac9, Ds9 and Ds6 to indicate their origins. The fragments cloned into the plasmids comprised 0.23 kb of the Wx locus sequence and the entire foreign insertion sequence in the mutant Wx locus for pAc9 and pDs9 and approximately 1.0 kb of the Wx locus sequence and the entire foreign insertion sequence for pDs6.

Figure 4:
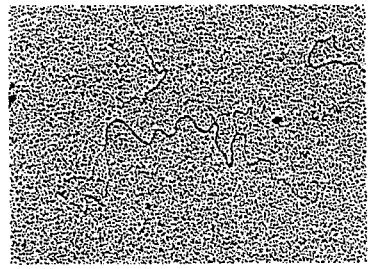
FIG. 4 shows an electron micrograph of a heteroduplex between linearized pAc9 and pDs9.
Figure 4:

Next, pAc9 and pDs9, i.e., plasmids containing the cloned Pst I fragments in opposite orientations, were linearized with Cla I, which cuts near the Pst I cloning site and then heteroduplexed. The thus obtained heteroduplexes and asymmetric single-stranded tails corresponding to the unpaired inverted plasmid sequences. The central portion of the heteroduplex was double-stranded, which indicated extensive homology between the insertion sequences (See FIG. 4). However, when the plasmids were subjected to restriction endonuclease mapping, it became evident that the pAc9 and pDs9 plasmids were not identical (See FIGS. 5a and 5b).

Figure 5:
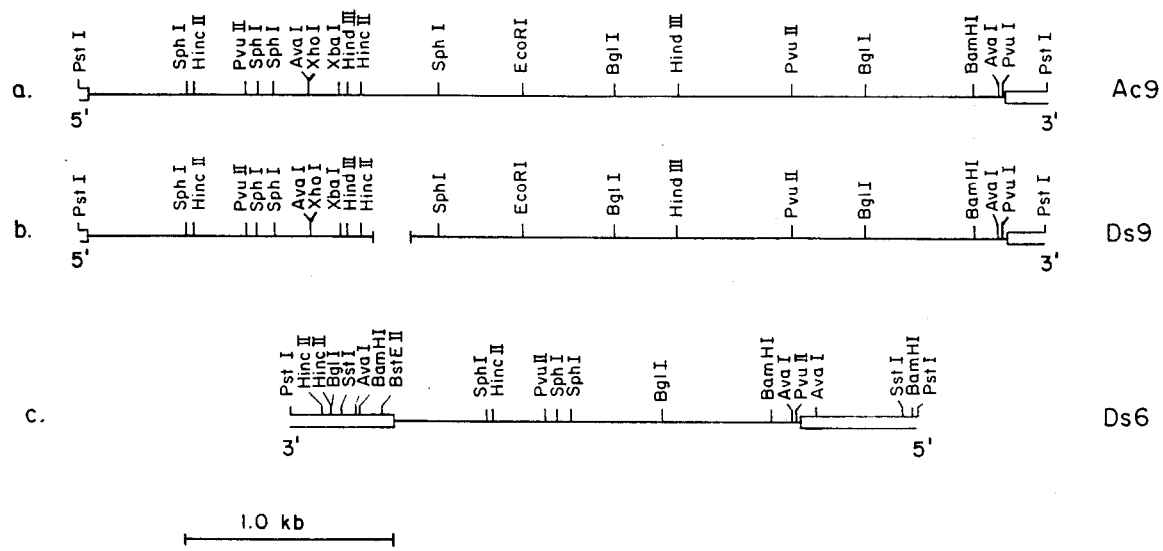
FIG. 5 shows restriction nuclease maps of Wx Pst I fragments containing the Ac9, Ds9 and Ds6 transposons.

In FIG. 5, the boxes represent the Wx locus sequence bounded by Pst I sites within which the insertion was located. The solid central lines represent the controlling element sequences. The orientation of the Wx locus fragment into which the elements have been inserted is indicated relative to the direction of transcription (See FIG. 1a). The cloned Pst I fragments in the two plasmids differed from each other by the absence from pDs9 of a sequence of less than 0.2 kb (represented by the interruption in (FIG. 5b) present near the center of the Ac element pAc9).

Figure 6:
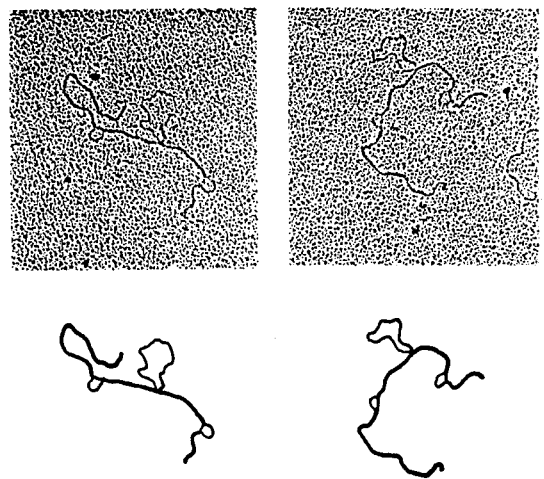
FIG. 6 shows an electron micrograph of a heteroduplex between pAc9 and pDs6.

Thus, the Acwx-m9 and wx-m9 strains had insertions at precisely the same site within the transcription unit. In addition, the insertions were virtually the same length and almost completely homologous. The insertion differed only by the absence of a short sequence from the center of the insertion in wx-m9 that was present in the Acwx-m9 insertion. Since the wx-m9 strain was a direct derivative of the Acwx-m9 strain, but behaved genetically like a Ds insertion mutation, this Ac-like insertion at the locus is the Ds element. The observation that the Ds9 element differed from the Ac9 element by the absence of a short central sequence suggests that the Ds element directly arose by deletion from the Ac element in the Acwx-m9 strain.

pDs6 and pAc9 were also linearized with Cla I, denatured, renatured and spread for electron microscopy and subjected to heteroduplex analysis as shown in FIG. 6. Since the insertion sites differed in Acwx-m9 and wx-m6, the terminal Wx sequences flanking the elements were not homologous and formed small loops at each end of the Pst I fragment in the plasmid. The central 2.0 kb sequence of the maize Pst I fragment in the pDs6 plasmid was entirely homologous to the termini sequences of the Ac element in pAc9. The central portion of the Ac element was not represented in the pDs6 plasmid and formed a large single-stranded loop. The loop was approximately centered within the double-stranded region. This indicated that the 2.0 kb insertion in the wx-m6 strain comprised 1.0 kb from each end of the Ac element. Additional evidence that the Ds6 element resembled the terminal of the Ac9 element was provided by the rsemblance between the restriction endonuclease cleavage site maps shown in FIG. 5a and FIG. 5c.

10. Composition of Ac and Ds Elements

The Ac and Ds elements did not appear to have extensive internal repetitions. The elements did not form fold-back or stem-loop structures after denaturation. The restriction nuclease maps of the elements (FIG. 5) likewise gave no evidence of either long internal or terminal redundancies. Indeed, there was a cluster of cleavage sites for Bam HI, Ava I and Pvu I very near one end of all of the elements that was not present at the other end. It has been determined by nucleotide sequencing that the Ac9 and Ds9 elements have 11 bp inverted terminal repetitions.

The presence of unique restriction endonuclease cleavage sites near one end of the Ac and Ds elements made it possible to determine the orientation of each of the three elements within the Wx locus. The Ac9 and Ds9 elements were both in the same orientation. This indicates that the Ds9 element is a direct deletional derivative of the Ac9 element that arose after insertion of the Ac element at the Wx locus. On the other hand, the Ds6 element was inserted in the opposite orientation to the Ac9 and Ds9 elements. Although the elements are shown in the same orientation in FIG. 5 for ease in comparing their internal structures, the orientation of the Wx locus Pst I fragments, within which they are inserted, is not the same and is indicated relative to the direction of transcription (See FIG. 1a).

11. Abundance of Ac-like Sequences and Ds-like Sequences in Maize DNA

In order to assess the abundance of sequences with homology to the Ac and Ds elements in maize genomic DNA, the Ava I fragment from the Ds6 element and a central Ava I-Eco RI fragment of Ac9 were used as probes in genomic blot hybridization experiments. Since the Ds element is homologous to the termini of the Ac element, it was used as a hybridization probe to assess the genomic representation of Ac element termini.

More specifically, the Ac probe used in the hybridization analysis was the left Ava I-Eco RI fragment from the center of the Ac9 element (See FIG. 5a) which includes the sequence deleted in the Ds9 element. This fragment was purified from an Ava I-Eco RI digest of pAc9 by preparative gel electrophoresis and labeled with $P^{32}$ by nick-translation (See Maniatis, T., Jeffrey, A. and Kleid, D. G., *Proc. Natl. Acad. Sci. USA* 72:1184–1188 (1975)) to a specific activity of $3 \times 10^8$ to $1 \times 10^9$ cmp/$\mu$g using $dATP^{32}$ and $dCTP^{32}$ (Amersham, specific activity 400 Ci/mmole) as labeled substrate.

The Ds probe used in the hybridization analysis was the Ava I fragment from pDs6 that included almost all of the 2.0 kb Ds6 element (See FIG. 5c), as well as a small amount of adjacent Wx sequence. This fragment was purified from an Ava I digest of pDs6 by preparative gel electrophoresis and labeled with $P^{32}$ by nick-translation (see Maniatis, T., Jeffrey, A. and Kleid, D. G., *Proc. Natl. Acad. Sci. USA* 72:1184–1188 (1975)).

Hybridization analysis of restriction endonuclease digests of genomic maise DNA using Southern blotting (See Southern, E. M., *J. Mol. Biol.* 98:503–517 (1975)) was conducted essentially as described by Fedoroff, N., Mauvis, J. and Chaleff, D., *J. Mol. App. Gen.* 2:11–29 (1983).

Genomic maize DNAs from strains having an active Ac element, i.e., Acwx-m9 and lacking an active Ac element, i.e., Wx, W23xK55 and wx-m9, were digested with BstE II, an enzyme that does not cleave within any of the isolated controlling elements. Included as controls in both experiments were amounts of recombinant phage DNA containing the cloned Acwx-m9 Bgl II fragment approximately equivalent to 1 or 5 genomic copies and *Xenopus laevis* DNA, which showed no homology to the probes used. The results are shown in FIG. 7.

Figure 7:
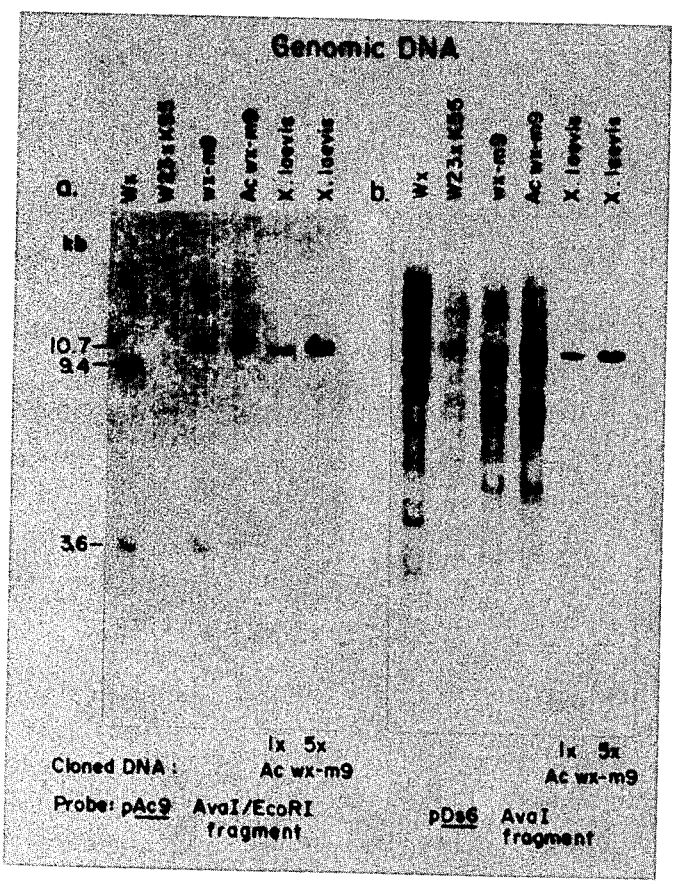
FIG. 7 shows an autoradiogram of a blot hybridization analysis of genomic maize DNAs digested with BstE II restriction nuclease.

It is evident from the autoradiograms shown in FIG. 7 that sequences homologous to both the Ds6 element and the central portion of the Ac9 element were present in all of the maize genomic DNAs examined, but not in *Xenopus laevis* DNA. Since the cloned 10.7 kb BstE II fragments of the recombinant phage DNA controls were present in equivalent amounts and hybridized with the Ac and Ds probes of the same extent, the hybridization of the maize DNAs to the two probes was directly comparable. The results obtained with Ds6 are similar to those reported by Geiser, M., et al, *EMBO J.* 1:1455–1460 (1982), using the Ds element associated with the Sh locus in the Ds-induced unstable sh-m5933 allele. This was not unexpected, since both Ds6 and the Ds element in the sh-m5933 allele originated from the same genetically defined Ds element (See McClintock, B. J., *Cold Spring Harbor Symposium Quant. Biol.* 16:13–47 (1951); McClintock, B., *Carnegie Inst. of Wash. Year Book* 51:212–219 (1952); and McClintock, B., *Carnegie Inst. of Wash. Year Book* 52:227–237 (1953)) and the two elements appear to be very similar or identical in sequence.

As FIG. 7b demonstrates, many sequences are homologous to the Ds element. That is, all of the strains had about 20–40 discrete BstE II fragments with homology to the Ds probe, some of which appeared to comprise multiple copies of a single fragment. However, the bands appeared on a continuous background of hybridizing sequences, suggesting the presence of many more copies of sequences with limited homology to the termini of the Ac element. Consistent with the existence of such sequences was the isolation of an 0.4 kb Ds element at the Adh I locus in maize that had very little homology to the Ds6 element, although it appeared to share an 11 bp terminal inverted repetition with the similar Ds element of the sh-m5933 allel (see Sutton, W. D., Ger-Pach, W. L., Schwartz, D. and Peacock, W. J., *Science*, 223:1265–1268 (1984)). These observations indicate that the Ds elements comprise a rather large family of sequences related to Ac elements. There is, in this regard, a strong parallel between the ubiquitous P elements of *Drosophila melanogaster* many of which are internally deleted, effective elements (See Rubin, G. M., *Mobile Genetic Elements*, J. Shapiro, Ed., (Academic Press) New York, pp. 329–361 (1983)). The structure of the Ds element at the Adh I locus (Sutton et al, Id.), however, suggests that a short terminal sequence from the Ac element suffices to confer Ds-like properties.

By contrast, as shown in FIG. 7a, maize DNA contains relatively few copies of sequences with homology to the central portion of the Ac9 element, although such sequences are present both in DNA from a strain that has a genetically active Ac element, i.e., Acwx-m9, and in strains that have either only Ds elements, i.e., Wx or wx-m9, or no detectable element, i.e., W23xK55. As FIG. 7a shows, the Acwx-m9 and wx-m9 strains contained a fragment that co-migrated with the cloned BstE II fragment, as well as 4 to 6 additional fragments ranging in size from 3.6 kb to 25 kb with homology to the center of the Ac element. The Wx strain from which the Wx Eco RI fragment was cloned contained no Ac elements, but had a Ds element proximal to the Wx locus. DNA from plants of this strain contained 4 major BstE II fragments with homology to the Ac probe, one of which appeared to be present in several copies. DNA from the W23xK55 hybrid contained 3 to 4 BstE II fragments with homology to the central region of the Ac element. Thus, sequences with homology to the central portion of the Ac9 element were much less prevalent in maize genomic DNA than were sequences homologous to the ends of the Ac9 element, suggesting that internally deleted elements resembling Ds6 are common components of the maize genome.

12. Structure of Ac-like Sequences in Genomic Maize DNA

The internal structure of the Ac-like sequences in genomic maize DNA identified above was investigated by analyzing genomic maize DNAs cleaved with enzymes that cut within the Ac9 element. When maize DNA from strains having an active Ac element, i.e., Acwx-m9, and lacking a genetically active Ac element, i.e., Wx, W23xK55 and wx-m9, were cleaved with Hind III, which yields a 1.6 kb fragment corresponding to the center of the cloned Ac9 element, multiple copies of the fragment were detected with the Ava I-Eco RI probe fragment from the center of the Ac9 element (See FIG. 8a).

In FIG. 8, the two right-hand lanes in each blot contained a mixture of Xenopus laevis genomic DNA and an amount of the cloned Acwx-m9 and wx-m9 Bgl II fragments equivalent to 5 genomic copies of the element as controls. DNA from strains that had or had recently had an active Ac element, i.e., Acwx-m9 and wx-m9, contained more copies of the 1.6 kb Hind III fragment than did strains that had not had a genetically active Ac element, i.e, Wx and W23xK55. It was estimated that the number of copies of the 1.6 kb Hind III sequence varied between 4 and 8 to 10 in the different DNAs analyzed. Only about half of the Ac-like sequences in each of maize DNAs analyzed yielded a 1.6 kb Hind III fragment. Most of the additional sequences with homology to the probe appeared on larger Hind III fragments, although all of the strains contained an additional Hind III fragment of about 1.0 kb with homology to the center of the Ac9 element. The shorter 1.4 kb Hind III fragment derived from the Ds9 element was detectable in wx-m9 maize DNA but was less abundant than the 1.6 kb fragment that was present in several copies.

Results similar to those obtained with Hind III were obtained when genomic maize DNAs were double digested with Ava I and Eco RI and probed with the left Ava I-Eco RI fragment from the center of the cloned Ac9 element. It was thus concluded that there were several copies of a sequence in all of the genomic maize DNAs examined whose internal structure resembled that of the cloned Ac9 element.

By contrast to the results described above, which indicated that at least half of the Ac-like sequences in the maize genome had a similar internal structure, the results of analogous experiments carried out with several other enzymes suggested that the genetically active Ac9 element at the Wx locus and its Ds9 derivative were structurally distinguishable from other genomic Ac-like sequences. Thus, for example, when the same genomic maize DNAs that gave multiple 1.6 kb Hind III fragments with homology to the Ac element (See FIG. 8a), were digested with Pvu II and Eco RI, only the Acwx-m9 DNA yielded a 1.3 kb Pvu II-Eco RI fragment that co-migrated with the corresponding fragment in the cloned Ac element (See FIG. 8b). None of the genomic DNAs from plants lacking a genetically detectable Ac element yielded a 1.3 kb Pvu II-Eco RI fragment with homology to the cloned Ac9 element. However, the wx-m9 DNA contained a 1.1 kb Pvu II-Eco RI fragement with homology to the Ac probe that co-migrated with the corresponding fragment in the cloned Ds9 element (See FIG. 8b). Thus, the Ac9 and Ds9 elements at the Wx locus were distinguishable from the other Ac-like sequences, all of which appeared on larger fragments in a Pvu II-Eco RI digest of maize DNAs.

Results similar to those obtained with Pvu II-Eco RI digests were also obtained after digestion of genomic maize DNA with Pcu II or Ava I alone with both Ava I and Pvu II. Hence, the differences between the Ac9 and Ds9 elements at the Wx locus and the other Ac-like sequences in the genome were not confined to a single restriction nuclease cleavage site nor to one end of the element. Thus, despite the similarity in the internal structure of the several Ac-like sequences present in all of the genomic maize DNAs examined, the single copy of the Ac element at the Wx locus was structurally distinguishable from the other Ac-like sequences. That is, certain restriction nuclease cleavage sites present in the cloned element could be detected in the elements inserted at Wx locus, but were either missing or insensitive to cleavage in the other Ac-like genomic sequences.

As demonstrated above, the Ac element in the Acwx-m9 mutant allele (See McClintock, B., *Carnegie Inst. of Wash. Year Book* 62:486-493 (1963)) is a 4.3 kb sequence inserted near the 3' end of the transciption unit. A Wx strain, i.e., the progenitor of the wx-m6 mutant strain, did not contain the sequence, which was also not present in a genomic fragment of the Wx locus cloned from a newly isolated Wx revertant of the Acwx-m9 allele, i.e., Wx9-rl. Reversion to the germinally stable Wx allele was accompanied by the loss of the Ac element from the locus, as determined by genetic criteria, as well as by the removal of the 4.3 kb insertion. Thus, the 4.3 kb insertion corresponds to the Ac element. It should be noted that although the initial restriction endonuclease analyses described above yielded a length of 4.3 kb for the Ac9 element, nucleotide sequencing analysis revealed that its exact length is 4563 nucleotides.

Wx locus fragments cloned from two Ds alleles, i.e., wx-m9 and wx-m6 (See McClintock, B., *Carnegie Inst. of Wash. Year Book* 52:227-237 (1952); and McClintock, B., *Carnegie Inst. of Wash. Year Book* 62:486-493 (1963)) also contained insertions within the transcription unit. The insertion in the fragment cloned from DNA of a plant carrying the wx-m9 allele was at the same site as the Ac element in the Acwx-m9 allele and was almost identical to it in structure. The Ds9 element in the wx-m9 allele differed from the Ac9 element in the Acwx-m9 allele, by a small, central deletion of less than 0.2 kb. Since the wx-m9 is a derivative of the Acwx-m9 allele (See McClintock, B., *Carnegie Inst. of Wash. Year Book* 62:486-493 (1963)), the Ds9 element was probably derived directly from the Ac9 element by a deletion mutation.

As exected from the experiments described by Shure, M., Wessler, S. and Fedoroff, N., *Cell* 35:225-233 (1983), the wx-m6 allele also yielded a Wx locus fragment with an insertion within the transcription unit. The insertion site was approximately 0.5 kb 5' to the insertion site in the Acwx-m9 and wx-m9 alleles. The 2.0 kb insertion was homologous to the ends of the Ac element. Moreover, its restriction endonuclease cleavage site map was indistinguishable from that of the Ds element identified in association with a complex Ds induced mutation at the Shrunken locus in maize (Courage-Tebbe, U., et al, *Cell* 34: 389-393 (1983)).

The structural differences between the Ac9 element and other Ac-like sequences in the genome are not well understood. While not desiring to be bound, several explanations are equally compatible with the observed structural differences. The possibility exists that the Ac9 and Ds9 elements at the Wx locus differ from other Ac-like sequences simply because they are inserted in a transcriptionally active region and therefore have different sequence modifications than at other sites. Another possiblity is that some or all of the Ac-like sequences detected above are inactive Ac elements that differ structurally from active Ac elements in a reversible way. It has been known for some time that there are cryptic controlling elements in maize genomes that can be activated by agents that cause chromosome damage (See McClintock, B., *Carnegis Inst. of Wash. Year Book* 45:176-186 (1946); McClintock, B., *Proc. Natl. Acad. Sci. USA* 36:344-355 (1950); McClintock, B., *Carnegie Inst. of Wash. Year Book* 49:157-167 (1959); Neuffer, M. G., *Genetics* 53:541-549 (1966); Bianchi, A., et al, *Maize Genetic Coop. News Lett.* 43:91 (1969); and Doerschug, E. B., *Theor. Appl. Genet.* 43:182-189 (1974)). These are probably distinct from Ds elements, since the conversion of an element initially identified as a Ds element to an Ac element has never been reported. However, it has been observed that an Ac element can be become reversibly inactive (See McClintock, B., *Carnegie Inst. of Wash. Year Book* 63:597-602 (1964); and McClintock, B., *Carnegie Inst. of Wash. Year Book* 64:527-534 (1965)). Such changes are reminiscent of those involved in several types of genetic interconversions in prokaryotes and lower eukaryotes (See Borst, P., *Mobile Genetic Elements*, J. Shapiro, Ed., (Academic Press) New York, pp. 622-659 (1983); Haber, S. E., *Mobile Genetic Elements*, J. Shapiro, Ed., (Academic Press) New York, pp. 560-619 (1983); and Silverman, M., et al, *Mobile Genetic Elements*, J. Shapiro, Ed., (Academic Press) New York, pp. 537-555 (1983)). The structural differences among the Ac-like sequences in genomic maize DNAs detected above may be associated with the state of Ac activity. The Ac element at the Wx locus in the Acwx-m9 strain is the only genetically active Ac element in the genome of that strain and the Ds9 element appeared to have been derived by a deletion mutation directed from the active element. Thus, the structural differences between the Ac9 element at the Wx locus and other Ac-like genomic sequences may be attributable to a rearrangement that originally activated the Ac9 element from a cryptic element.

The method described in detail above which resulted in the isolation of the Ac and Ds transposons has been used for the isolation of other Ac transposons and can be extended to other maize transposons such as the Mp transposon, believed to be similar or identical to the Ac transposon (see Barclay, P. C. and Brink, R. A., *Proc. Natl. Acad. Sci. USA* 40:1118-1126 (1954)), the Suppressor-mutator (Spm) transposon, as well as to other maize transposons (see Fedoroff, N., *Mobile Genetic Elements*, J. Shapiro, Ed., (Academic Press) New York, pp 1-63 (1983) and Fincham, J. R. S. and Sastry, G. R. K., *Ann. Rev. Genet.* 8:15-50 (1974).

EXAMPLE 2

Use of Isolated Transposons to Identify and Isolate Genes

The above-described isolation of the Ac and several Ds transposons has allowed for the use of the cloned elements to further isolate other maize loci with mutations caused by these elements (See Fedoroff N., Wessler, S. and Shure, M., *Cell* 35:235-242 (1983); Geiser, M., Weck, E., Döring, H.-P., Werr, M., Courage-Tebbe, U., Tillmann, E. and Starlinger, P., *EMBO J.* 1:1455-1460 (1983); and Courage-Tebbe, U., Doring, H.-P., Fedoroff, N. and Starlinger, P., *Cell* 34:383-393 (1983)) because the ends of the Ac transposons are abundantly represented in the maize genome, while the center of the element is not (See Fedoroff, N., Wessler, S. and Shure, M., *Cell* 35:235-242 (1983); and Geiser, M., Weck, E., Döring, H.-P., Werr, W., Courage-Tebbe, U., Tillmann, E. and Starlinge, P., *EMBO J.* 1:1455-1460 (1983)). Thus, genetically active Ac transposons appear to have a unique structure which can be used to identify a gene with an Ac insertion mutation.

In this example, the gene encoding the Bronze locus (hereinafter "Bz") is identified and isolated.

The enzyme UDPglucose:flavonoid glucosyl transferase (hereinafter "UFGT") catalyses the 3-0-glucosylation of flavonols and anthocyanidins (See Larson, R. L., *Phytochem.* 10:3073-3076 (1976); and Larson, R. L. and Lonergan, C. M., *Planta* 103:361-364 (1972)). Studies on strains with recessive mutations at the Bz locus have provided evidence that the locus encodes UFGT (See Larson, R. L. and Coe, E. H., Jr., *Biochem. Genet.* 15:153-156 (1977); Dooner, H. K. and Nelson, O. E., *Proc. Natl. Acad. Sci. USA* 74:5623-5627 (1977)). Expression of the Bz-encoded UFGT has also been investigated in strains with unstable mutations caused by insertion of transposable controlling elements (See Dooner, H. K. and Nelson, O. E., *Proc. Natl. Acad. Sci. USA* 74:5623-5627 (1977); Dooner, H. K., *Cold Spring Harbor Symp. Quant. Biol.* 45:467-462 (1980); McClintock, B., *Carnegie Inst. Washington Year Book* 50:174-188 (1961); McClintock, B., *Carnegie Inst. Washington Year Book* 54:245-255 (1955); McClintock, B., *Carnegie Inst. Washington Year Book* 55:323-332 (1956); and McClintock, B., *Carnegie Inst. Washington Year Book* 61:448-461 (1962)). The results of such studies suggest that transposon mutuations can alter both the structure of the enzyme and the developmental timing of gene expression.

Although the protein encoded by the Bz locus comprises approximately 0.1% of the aleurone protein at maturity (Fedoroff, N. and Mauvais, J., *Maize Genet. Coop. Newsletter* 56:8-10 (1982)), efforts to identify the newly-synthesized protein either among proteins labeled in vivo or among in nitro translation products of aleurone mRNA by immunological means have not been successful. The present invention provides a method for cloning the Bz locus, based on its association with a transposable controlling element. Since it was known from blot hybridization experiments, described above, that there were relatively few copies of genomic DNA sequences with homology to the center of the cloned Ac9 transposon, a fragment subcloned from the center of the element was used as a probe for the isolation of homologous fragments from a genome that has an Ac insertion mutation at the Bz locus. From among the cloned genomic fragments, those that contained an Ac-like structure were selected and homology of the flanking sequences to the Bz locus was tested. By this procedure, which is described in detail below, a DNA fragment homologous to the Bz locus was identified and used to clone the locus from a non-mutant maize strain.

1. Isolation and Cloning of Genomic DNA Fragments

DNA was isolated from immature tassels of 6-week old plants that were homozygous for the Acbz-m2 allele, which had an Ac transposon inserted at the Bz locus as described above (See McClintock, B., *Carnegie Inst. Washington Year Book* 50:174-181 (1951); and Shure, M., Wessler, S. and Redoroff, N., *Cell* 35:235:242 (1983)). Plants were made homozygous for the Acbz-m2 allele by outcrossing to Bz plants of different genetic backgrounds and self-pollinating the resulting heterozygous progeny. Bz revertants were either directly selected as single kernels on ears of Acbz-m2 homozygotes or isolated from a derivative allele, designated bz-m2-Dl (See McClintock, B., *Carnegie Inst. Washington Year book* 61:448-461 (1962)), that behaved genetically as a Ds mutation. That is, the transposon was no longer capable of autonomous transposition, but transposed in the presence of an Ac transposon (See McClintock, B., *Carnegie Inst. Washington Year Book* 61:448-461 (1962)).

Bgl II or Bam HI fragments of genomic DNA were cloned in the λ EMBL4 vector as described above to produce λAcbz-m2 clones.

2. Probing Cloned Fragments with DNA Segments from the Center of a Transposon Derived from Maize The above-mentioned recombinant phages were screened with a plasmid containing the 1.6 kb Hind III fragment representing the center of the Ac9 transposon inserted into pKP32 (hereinafter "pAcHl.6") (See FIG. 5a). The screening was carried out as described in Benton, W. D. and Davis, R. W., *Science* 196:180-182 (1977) using pAcHl.6 labeled with $P^{32}$ by nick-translation (See Maniatis, T., et al, *Proc. Natl. Acad. Sci. USA* 72:1184-1188 (1975)).

Twenty-five clones containing maize DNA fragments with homology to the center of the Ac element, i.e., with homology to pAcHl.6, were identified; 24 were Bgl II fragments and one was a Bam HI fragment. The λAcbz-m2 clones are designated by the number of the isolate. Clones λAcbz-m2-7a, 7b and 1-20 containing Bgl II fragments and clone λAcbz-m2-1b contains a Bam HI fragment of maize DNA.

3. Structure of the Ac-like Sequences in the Cloned Fragments

The structure of the Ac-like sequences in the cloned fragments was then investigated by probing restriction endonuclease digests of the cloned fragments with pAcHl.6 (See Fedoroff, N., Wessler, S. and Shure, M., *Cell* 35:235-242 (1983)) noting that the Ac9 element contains a single central Eco RI site, which is flanked by 2 Hind III sites and 2 Pvu II sites (See FIG. 5). The results are shown in FIG. 9.

In FIG. 9, recombinant phage DNAs from the indicated isolates were cut with Eco RI (See FIG. 9a) and Pvu II (See FIG. 9b) and fractionated on agarose gels. The DNA was denatured, transferred to nitrocellulose and hybridized with $^{32}P$-labeled pAcHl.6. The sizes of marker fragments included in the gel are indicated. As FIG. 9 demonstrates, when phage DNAs containing maize inserts with homology to the internal Hind III fragment of Ac9 were digested with Eco RI, most, but not all, yielded two Eco RI fragments homologous to the 1.6 kb Hind III fragment of Ac9 (See FIG. 9a).

On the other hand, only a few of the cloned fragments, yielded a Pvu II fragment with homology to pAcHl.6 that had the mobility of the 2.6 kb Pvu II fragment of Ac9 (See FIG. 9b, arrow). Of the 25 fragments cloned from DNA of an Acbz-m2 homozygote, only 6 yielded internal Pvu II fragments homologous to the Ac9 transposon that co-migrated with the internal fragments derived from the cloned element.

To determine which of the cloned fragments were identical and represented reisolates of the same sequence, the fragments were analyzed for the location of several restriction sites in the DNA flanking the Ac-like sequence. Phage DNAs were cleaved with Pvu II, Ava I and Taq I and probed with a labeled fragments corresponding to the entire Ac9 transposon, i.e., pAc9. The results are shown in FIG. 10.

In FIG. 10, recombinant phage DNAs from the indicated isolates, i.e., λAcbz-m2-1b, 6, -7a, -13, and -14, and λAcwx-m9 were digested with Pvu II (See FIG. 10a), Ava I (See FIG. 10b) and Taq I (See FIG. 10c), fractionated on agarose gels, denatured and transferred to nitrocellulose filters. The filters were hybridized either with a $^{32}P$-labeled plasmid containing the Ac9 transposon, i.e., pAc9, or with isolated fragments representing the middle and ends of the Ac9 transposon.

Pvu II cuts twice within the Ac9 transposon, yielding a 2.6 kb fragment representing the central portion of the transposon, and two additional fragments with homology to Ac that extend from within the transposon to the first Pvu II site in the adjacent DNA. All of the clones analyzed, whose results are shown in FIG. 10a, contained the 2.6 kb fragment corresponding to the center of the Ac transposon. In clones λAcbz-m2-6 and λAcbz-m2-8a, the two additional Pvu II fragments that are homologous to the ends of the element have the same mobility. Because similar results were obtained with several enzymes, clones λAcbz-m2-6 and λAcbz-m2-8a represented reisolates of the same genomic fragment. The flanking Pvu II sites in clone λAcbz-m2-14 were at a different distance from the internal sites than they were in the genomic fragment represented in clones λAcbz-m2-6 and λAcbz-m2-7a.

The results of a similar experiment in which the genomic fragments were digested with Ava I are shown in FIG. 10b and yielded similar results. Since Ava I cuts very near the right end of the Ac transposon, Ava I digests contained only two fragments with significant homology to Ac transposon. One was a 3.5 kb internal fragment and the other extended from the Ava I site approximately 1.0 kb from the left end of the element to the first Ava I site in the flanking DNA. Clones λAcbz-m2-14 and λAcbz-m2-7a shared the internal fragment, but had different flanking fragments. Thus, the Ac-like sequence in cline λAcbz-m2-14 was flanked by different genomic sequences than it was in the fragment present in clones λAcbz-m2-6 and λAcbz-m2-7a.

Evidence that the Ac-like sequences in λAcbz-m2-7a and λAcbz-m2-14 were very similar to each other and to those of the previously-isolated Ac-9 transposon was provided by the results of the Taq I digest shown in FIGS. 10c. Since Taq I cuts very near the ends of the Ac9 transposon, as well as near the center of the transposon, all of the fragments detectable in a Taq I digest with probes derived from Ac9 are fragments from within the Ac9 transposon. All 3 large internal fragments were identical in clones λAcbz-m2-7a and λAcbz-m2-14 and the fragments had the same mobility a those derived from the Ac9 transposon inserted in a fragment of the Wx locus (See FIG. 10c). By these criteria, clones λAcbz-m2-7a and λAcbz-m2-14 contained internal Ac-like sequences indistinguishable from those present in Ac9 and they were flanked by different genomic sequences.

Also included in FIG. 10 are the results of blot hybridization analysis of clones λAcbz-m2-1b and λAcbz-m2-13. Clone λAcbz-m2-1b contained a Bam HI fragment, while clone λAcbz-m2-13 contained a Bgl II genomic fragment. Since Bam HI cuts within the Ac9 transposon (See FIG. 5), a Bam HI clone containing an Ac sequence extends from the Bam HI site within the element to the first Bam HI site flanking the element on the left. If the flanking sequence is the same as it is in one of the Bgl II clones, then the fragments should contain similar flanking sequences on one side of the element. By this criterion, the sequence represented in clone λAcbz-m2-1b appeared to be the same as that represented in clones λAcbz-m2-6 and λAcbz-m2-7a. Thus, in both the Pvu II and Ava I digests, clone λAcbz-m2-1b had one flanking fragment that had an identical mobility to one of the flanking fragments in clones λAcbz-m2-6 and λAcbz-m2-7a. Hence, the Bam HI clone contained Ac in the same genomic sequence as clones λAcbz-m2-6 and λAcbz-m2-7a. Clone λAcbz-m2-13, which yielded a central fragment with homology to Ac that co-migrated with that of Ac9, was distinguishable from the Ac9 transposon by the lengths of both the left and right large Taq I fragments. Both terminal Taq I fragments represented in the Ac-like sequence of clone λAcbz-m2-13 were shorter than the analogous fragments in the Ac9 transposon and the Ac-like sequences of clones λAcbz-m2-7a and λAcbz-m2-14.

Accordingly, of the 6 newly-isolated genomic DNA fragments that initially yielded internal fragments that co-migrated with those of the Ac9 transposon, 4 proved to be reisolates of the same sequence. Of the 3 cloned fragments with Ac-like sequences inserted in different genomic sequences, only two, i.e., λAcbz-m2-7a and λAcbz-m2-14, had an internal structure indistinguishable from that of the previously-isolated Ac9 transposon by the criteria employed.

4. Identification of Subclones Containing the Bz Locus

In order to determine whether the sequences flanking the Ac-like transposon in the cloned genomic fragments were derived from the Bz locus, fragments adjacent to the Ac-like sequence were subcloned in pUC8 (See Vieira, J. and Messing, J., *Gene* 19:259-268 (1982)) and used to probe genomic DNA from plants with different mutations at the Bz locus. The subclone used as the genomic probe represents a Pst I fragment located about 1.0 kb to the left of the Ac-like sequence in clone λAcbz-m2-7a.

The first genomic fragment analyzed was the one represented in clones λAcbz-m2-1b, λAcbz-m2-6 and λAcbz-m2-7a (See FIG. 10). Pst I and Pst I-Eco RI fragments adjacent to the Ac-like sequence in λAcbz-m2-7a on the left and right were subcloned in plasmid pUC8 at the Pst I site therein and tested for homology to reiterated maize genomic sequences by blot hybridization of the plasmid to total maize DNA labeled with $^{32}P$ by nick-translation (See Maniatis, T., Jeffrey, A. and Kleid, D. G., *Proc. Natl. Acad. Sci. USA* 72:1184-1188 (1975); Bell, G. I., Pictet, R. and Rutter, W. J., *Nucl. Acids. Res.* 8:4091-4109 (1982); and Southern, E. M., *J. Mol. Biol.* 98:503-517 (1975)). A 1.6 kb Pst I fragment that did not hybridize to repetitive DNA was identified. A plasmid containing the 1.6 kb Pst I fragment from λAcbz-m2-7a inserted into pUC8 (hereinafter "pAcl27P1"), was used to probe digests of genomic DNA plants of known constitution at the Bz locus. The results are shown in FIG. 11.

In FIG. 11, DNA from plants that were homozygous for the Acbz-m2 allele of the Bz locus yielded a single 10.8 kb Bgl II fragment with homology to the subcloned Pst I fragment from λAcbz-m2-7a. DNA from a plant that was heterozygous for the mutant and revertant alleles yielded both a 6.3 kb and a 10.8 kb Bgl II fragment. The Bgl II fragments detected in the plants with an Ac insertion different in length from those detected in plants carrying either revertant Bz alleles or a non-mutant Bz allele by 4.5 kb, i.e., the length of the Ac transposon (See FIG. 5). Hence, plants that differed from each other by virtue of a genetically-defined Ac insertion mutation yielded DNA fragments with homology to the probe that differed in length from each other by the length of the Ac element.

Moreover, DNA from plants that were homozygous for the sh bz-x2 and sh bz-x3 alleles (See Mottinger, J. P. *Genetics* 64:259:271 (1970)) did not give a Bgl II fragment with homology to the probe. Both alleles have previously been shown to lack sequences homologous to the adjacent *Shrunken locus* (See McCormick, S., Mauvais, Jr. and Fedoroff, N., *Mol. Gen. Genet.* 187:494-500 (1982)), indicating that these alleles are deletion mutations. Hence, these mutations represent deletions of both the Sh and Bz loci. Taken together, the results of genomic blot hybridizations clearly demonstrate that the Pst I fragment adjacent to the Ac-like sequence in clone λAcbz-m2-7a is a fragment of the Bz locus.

5. Isolation of the Bz Locus

Figure 12:
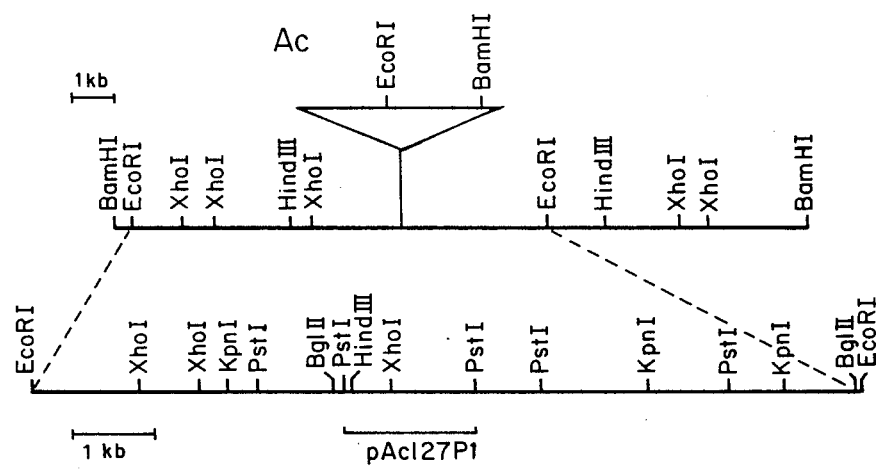
FIG. 12 shows a restriction nuclease map of a Bam HI fragment of the Bz locus. The site of Ac insertion in the Acbz-m2 allele is indicated, as is the location of the Pst I fragment in pAc127Pl.

The pAcl27P1 plasmid was used as a probe to isolate a Bam HI fragment of the Bz locus from DNA of a strain that was homozygous for a non-mutant Bz allele, i.e., a nonmutant Bz allele present in a strain provided by B. McClintock. As expected, the fragment was not interrupted by an Ac-like sequence. A restriction endonuclease cleavage site map of the locus is shown in FIG. 12. The site of Ac insertion in the Acbz-m2 allele is indicated, as is the location of the sequence represented in the pAcl27P1 plasmid.

6. Isolation of Other Maize Genes

The method described in this example can be extended to the isolation of additional maize genes that have Ac insertion mutations. At present, these include the P and the R loci of maize, which have mutations caused by the Mp transposon that is genetically indistinguishable from the Ac element (See Barclay, P. C. and Brink, R. A., *Proc. Nat'l. Acad. Sci. USA* 40, 1118-1126 (1954)).

A method for generating new transposon mutations at desired loci, based on the mechanism of Mp transposition has been recently developed. This method involves bringing the target or recipient locus (i.e., the locus into which it is desired to insert the transposon) near the donor locus (i.e., the locus at which the element currently resides) by means of reciprocal translocations. Progeny of plants having the transposon donor and recipient loci in close juxtaposition are then screened for insertions of the element into the donor locus. This process will generate new transposon insertion mutations at loci that have not yet been isolated. Thus, the genetic and molecular methods described above make it possible to isolate mutations in agronomically important genes and clone these genes, with the ultimate objective of changing the genes in beneficial ways and reintroducing them into plants.

EXAMPLE 3

Use of Isolated Transposons to Insert Desired Gene Sequences into Plants in a Heritable Manner The above-described isolation of the Ac and several Ds transposons has allowed for the development of gene transfer vectors containing these transposons for use in inserting desired gene sequences into plants in a heritable manner. The insertion of desired sequences into plants can be conducted by the transformation of plants, cultured plant cells or plant protoplasts as described below.

1. Gene Transfer Vectors for Transformation of Maize Plants

Mutations caused by defective transposons, such as the Ds9 transposon described above, are stable in the absence of an Ac transposon in the plant. Thus, a plant that is homozygous for a Ds mutation that affects a gene whose product catalyzes one of the steps in, for example, anthocyanin pigment biosynthesis is unable to synthesize the pigment. As a result, the plant is green and the aleurone layer of the kernels produced by such a plant are colorless. However, when an Ac transposon is present, this plant shows sectors of deeply pigmented plant and aleurone tissue. By introducing a cloned Ac transposon, e.g., pAc9, into a plant that is homozygous for a Ds mutation, but lacks an Ac transposon, and if the introduced Ac transposon is expressed, the plant or kernel would show sectors of deeply pigmented tissue.

The pDs9 plasmid, whose structure is virtually identical to that of the pAc9 plasmid, except that the cloned transpson lacks a 0.2 kb sequence present near the center of the Ac transposon (See Fedoroff, N., Wessler, S. and Shure, M., Cell 25:235-242 (1983)) can be used as an excellent control for these experiments, since the Ds transposon in this plasmid is known, from genetic experiments, to be incapable of promoting either its own transposition or the transposition of other Ds transposons.

Another type of gene transfer vector that can be constructed is one that consists of a modified maize transposon containing a maize gene whose expression can be monitored readily after introduction into the maize plant. Since it is known that the short repeated sequences at the ends of the transposon are recognized by the enzymes that catalyse transposition, this vector must contain sequences from each end of the transposon. Such a vector can easily be derived from pAc9 by in vitro mutagenesis. For example, pAc9 can be linearized with Eco RI and most of the internal sequence of the Ac transposon can be removed by digestion with nuclease Bal 31 (BRL). The plasmid can then be converted into a cloning vector by introducing commercially available polylinkers, i.e., polynucleotides containing multiple restriction endonuclease cleavage sites, before religation of the plasmid. The modified plasmid can then be further modified by the insertion of a maize marker gene, e.g., the Bz gene, whose isolation is described above. The Wx locus and the A locus are other examples of marker genes useful in the present invention. This modified plasmid is what is meant by a "derivative of a transposon derived from maize" described above. Since, as described above, the Bam HI fragment of the Bz locus is believed to contain the entire coding sequence, this fragment can be inserted into a plasmid containing the terminal sequences of the Ac transposon using the Bam HI site in the polylinker to position the Bz fragment between the Ac transposon termini. Although the Bz locus is the only gene affecting anthocyanin biosynthesis that has so far been cloned, other loci encoding enzymes involved in anthocyanin biosynthesis can also be employed in the present invention.

The Bz locus is a desired locus to be employed in the present invention since there exist two strains, i.e. sh bz-x2 and sh bz-x3, that have deletion mutations at the Bz locus. Thus, successful introduction of the Bz locus can be evaluated visually by the development of pigments due to the presence of the normal allele of the Bz locus. Insertion of the Bz locus can be checked by blot hybridization analysis, using cloned fragments of the Bz locus to detect the presence of introduced genes and determine whether it has been integrated into the plant's genome.

The above-described transposons will not catalyse their own transposition and thus have to either be introduced into plants that have structurally intact Ac transposons or introduced together with an intact cloned Ac transposon or other transposon possessing an active transposase. That is, the Ac transposon provides a trans-acting substance, i.e. transposase, required for transposition of the Ds transposition. In the presence of the active Ac transposon, the modified Ds transposon containing the foreign genes will transpose from the plasmid into the genome of the plant. The pAc9 plasmid, described above can be used to provide the trans-acting transposition function that is needed to promote the transposition of the composite transposon from its plasmid vehicle into the DNA of plants that lack an active Ac transposon.

Other combinations of modified and unmodified transposons other than those used as examples can also be used to introduce genes into plants by the methods described herein.

2. Gene Transfer Vectors for Transformation of Cultured Maize Plant Cells

Although it is not yet possible to regenerate whole maize plants from single protoplasts, a maize cell line now available (See Chourey and Zusareski, Theoret. Appl. Gen. 59:341-344 (1981)) can be converted to protoplasts capable of regenerating cell walls and continuing growth as cultured cells. Gene transfer vectors used for transforming cultured plant cells must contain a marker whose expression can be selected for. An example of such a marker is a gene that is capable of conferring antibiotic resistance. Such markers have been developed for the plant gene transfer vectors derived from Agrobacterium Ti plasmid (See Herrera-Estrella, L., et al, EMBO J. 2:987-995 (1983)). More specifically, a composite gene comprising a coding sequence for the bacterial gene that confers resistance to kanamycin under the control of a plant promoter has been used as a marker. The resulting hybrid gene can then be incorporated into a maize transposon as described above. Other hybrid plasmids can be made, using promoters from cloned maize genes to assure expression of the drug-resistance marker in the maize cells. The composite transposon contained in the drugresistance gene can then be introduced into isolated maize protoplasts and cells regenerated from the protoplasts can be tested for acquisition of drug-resistance.

3. Gene Transfer Vectors for Transformation of Other Plants and Plant Cells

The gene transfer vectors described above are those most suitable for the transformation of maize plants and plants tissue culture cells. However, the maize Ac and Ds transposons, as well as other maize transposons such as the Mp and Spm transposons, can be adapted to serve as gene transfer vectors in other plants, including both monocots, e.g. wheat, rye and other cereal grains, and dicots e.g. tobacco, tomato, petunia, which are either agronomically or scientifically important as experimental organisms for the study of plant gene expression. The Ac transposon can be introduced into tobacco plants via a modified *Agrobacterium tumefaciens* Ti plasmid carrying Ac9. The activity of the transposon can be tested by introducing, by the procedures described above, a selectable marker, e.g. drug resistance, carrying a Ds mutation constructed in vitro. The activity of the resident Ac transposon, or a cloned Ac transposon that is co-introduced with the mutant drug-resistance marker can be judged by the appearance of drug resistance in some transformed plants or plant cells. Drug resistant cells arise by the Ac-stimulated excision of the Ds transposon from the drug-resistance gene.

In order to promote expression of a maize derived transposase in other plants, it is possible to modify the sequence of the transposon, since the entire nucleotide sequence of the Ac9 transposon has been determined and subjected to computer analysis. That is, it has been established that the transposon contains two major sequences capable of encoding proteins and that one of these sequences corresponds to the transposase gene, i.e. gene that is required for the transposon to promote either its own transposition or that of a related Ds transposon. Each coding sequence is preceded by short nucleotide sequences typical of those that signal initiation of transcription. By replacing the maize transciption initiation signals with transcription initiation signals from genes that are known to work in tobacco, (See Herrera-Estrella, L., et al., *EMBO J.* 2:987-995 (1983)), the resulting modified transposon's expression can be promoted in, e.g. tobacco, and employed to insert desired gene sequences into plants other than maize in a heritable manner.

While this invention has been described in detail and with reference to specific embodiments thereof, it will be apparent to one skilled in the art that various changes and modifications could be made therein without departing from the spirit and scope thereof.

I claim:

1. An essentially pure transposon isolated from maize, wherein said transposon is Ac.

2. The essentially pure transposon isolated from maize of claim 1, wherein and Ac is Ac9.

3. A derivative of an essentially pure transposon isolated from maize, wherein said derivative comprises a transposon isolated from maize having a marker gene inserted between the terminal sequences thereof, wherein said transposon is Ac.

4. The derivative of an essentially pure transposon isolated from maize of claim 3, wherein said Ac is Ac9.

5. The derivative of claim 3, wherein said marker gene is selected from the group consisting of the Wx locus, the A locus, the Bz locus and a drug-resistance locus.

6. A cloning vector comprising a cloning vehicle having integrated therein a transposon isolated from maize or a derivative thereof, wherein said derivative comprises a transposon isolated from maize having a marker gene inserted between the terminal sequences thereof, wherein said transposon is Ac.

7. The cloning vector of claim 6, wherein said cloning vehicle is selected from the group consising bacterial plamids, bacteriophage DNAs, plant viral DNAs and animal viral DNAs.

8. The cloning vector of claim 7, wherein said bacterial plasmids are selected from the group consisting of pK32, pBR322, pBR325, and pUC8.

9. The cloning vector of claim 6, wherein said Ac is Ac9.

10. The cloning vector of claim 6, wherein said cloning vector is pAc9.

11. A method for identifying and isolating genes from a plant comprising:
    (1) isolating genomic DNA from a plant or a plant cell carrying a transposon insertion mutation at the locus to be isolated;
    (2) cloning fragments of the genomic DNA of Step (1);
    (3) probing the cloned fragments of Step (2) with DNA sequences from a transposon isolated from maize so as to select for cloned fragments homologous to said transposon, wherein said transposon is Ac;
    (4) subcloning the sequences flanking said transposon from the clone selected out in Step (3);
    (5) probing genomic DNA fragments from plants that carry mutant and non-mutant alleles of the locus to be isolated with the subclone of Step (4) so as to identify subclones containing the gene of interest;
    (6) cloning genomic DNA fragments from plants that carry a non-mutant allele of the locus to be isolated; and
    (7) probing the resulting clones of Step (6) with the subclone of Step (5) so as to isolate the locus.

12. The method of claim 11, wherein said Ac is Ac9.

13. The method of claim 11, wherein said plant or plant cell is a plant or plant cell into which a cloned transposon isolated from maize has been introduced, or progeny thereof.

14. A method for incorporating desired genes into the genome of a plant in a heritable manner comprising:
    (1) cloning a gene to be transferred into a transposon isolated from maize or a derivative thereof, wherein said derivative comprises a transposon isolated from maize having a marker gene inserted between the terminal sequences thereof and wherein said transposon is Ac;
    (2) incorporating, into a plant, plant cell or plant protoplast:
        (a) the resulting transposon product of Step (1); and
        (b) a transposon possessing an active transposase, so as to cause the gene to be transferred to be affirmatively incorporated into the genome of the plant in a heritable manner.

15. The method of claim 14, wherein said Ac is Ac9.

16. The method of claim 14, wherein said derivative comprises a transposon isolated from maize having a marker gene inserted between the terminal sequence thereof.

17. The method of claim 16, wherein said marker gene is selected from the group consisting of the Wx locus, the A locus, the Bz locus and a drug-resistance locus.

18. The method of claim 14, wherein said plant is a monocotyledon.

19. The method of claim 14, wherein said plant is a dicotyledon.

20. The method of claim 14, wherein said plant is selected from the group consisting of maize, wheat, rye, tobacco, tomato and petunia.

* * * * *

UNITED STATES PATENT AND TRADEMARK OFFICE
CERTIFICATE OF CORRECTION

PATENT NO. : 4,732,856

DATED : March 22, 1988

INVENTOR(S) : Nina V. Fedoroff

It is certified that error appears in the above-identified patent and that said Letters Patent is hereby corrected as shown below:

At line [75], the inventor should read --Nina V. Fedoroff-- not "Nina V. Federoff".

Signed and Sealed this

Second Day of August, 1988

Attest:

DONALD J. QUIGG

Attesting Officer

Commissioner of Patents and Trademarks